United States Patent [19]

Glasky

[11] Patent Number: 5,091,432
[45] Date of Patent: Feb. 25, 1992

[54] 9-SUBSTITUTED HYPOXANTHINE BI-FUNCTIONAL COMPOUNDS AND THEIR NEUROIMMUNOLOGICAL METHODS OF USE

[76] Inventor: Alvin J. Glasky, 9902 Brier La., Santa Ana, Calif. 92705

[21] Appl. No.: 500,789

[22] Filed: Mar. 28, 1990

[51] Int. Cl.$^5$ .................... A61K 31/52; C07D 473/00
[52] U.S. Cl. .................................. 514/262; 544/265; 544/276
[58] Field of Search ...................... 544/277, 276, 265; 514/262

[56] References Cited

U.S. PATENT DOCUMENTS

| | | | |
|---|---|---|---|
| 3,321,369 | 5/1967 | Glasky et al. | 167/65 |
| 3,438,968 | 4/1969 | Glasky | 260/211.5 |
| 4,221,794 | 9/1980 | Simon et al. | 544/265 |
| 4,221,909 | 9/1980 | Simon et al. | 544/265 |
| 4,221,910 | 9/1980 | Giner-Sorolla | 544/265 |
| 4,728,605 | 3/1988 | Fudenberg et al. | 435/29 |
| 4,952,693 | 8/1990 | Sircan et al. | 544/277 |

OTHER PUBLICATIONS

Chemical Abstracts—Registry File search of general structures (Annex 1).
Chemical Abstracts—Registry File search of publications related to structures located in Annex 1 search results (Annex 2).
Chemical Abstracts—Registry File search of 9H-Purine-9-propanoic acid derivatives with antiviral activities (Annex 3).
Chemical Abstracts—Registry File search of adenosine analogs (Annex 4).
Computer generated listing of Applicant's patents relating to memory enhancement, learning enhancement, and nucleic acids.
Computer generated listing of patents relating to Isoprinosine (Inosiplex).
Computer generated listing of immunomodulator patents assigned to Newport Pharmaceuticals.
American Chemical Society Chemical Abstracts Structural Search.
Kenneth A. Jacobson, "Chemical Approaches to the Definition of Adenosine Receptors", Adenosine Receptors, pp. 1-26, 1988.
Appel and McManaman, "Is a Breakdown of the Blood-Brain Barrier Cause or Effect?", Neurobiology of Aging, vol. 7, pp. 512-514, 1986.
MacDonald et al., "Immunological Parameters in the Aged and in Alzheimer's Disease", Clin. Exp. Immunol. (1982), vol. 49, pp. 123-128.
Miller et al., "Immunological Studies in Senile Dementia of the Alzheimer Type: Evidence for Enhanced Suppressor Cell Activity", Annals of Neurology, vol. 10, No. 6, pp. 506-510, Dec. 1981.
Stefansson et al., "Neuroimmunology of Aging", Clinical Neurology of Aging, pp. 76-94, 1984.
Weitkamp et al., "Alzheimer Disease: Evidence for Susceptibility Loci on Chromosomes 6 and 14", American Journal of Human Genetics, 35:443-453, 1983.
Ordy et al., "An Animal Model of Human-Type Memory Loss Based on Aging, Lesion, Forebrain Ischemia, and Drug Studies With the Rat", Neurobiology of Aging, vol. 9, pp. 667-683, 1988.
Ritzmann et al., "Blockage of Narcotic-Induced Dopamine Receptor Supersensitivity by Cyclo (Leu-Gly)", Proc. Natl. Acad. Sci. USA, vol. 76, No. 11, pp. 5997-5998, Nov. 1979.
Tsang et al., "Modulaton of T- and B-Lymphocyte Functions by Isoprinosine in Homosexual Subjects with Prodromata and in Patients with Acquired Immune Deficiency Syndrome (AIDS)", Journal of Clinical Immunology, vol. 4, No. 6, pp. 469-478, 1984.
Hadden et al., "Levamisole and Inosiplex: Antiviral Agents with Immunopotentiating Action", Annals of the New York Academy of Sciences, vol. 284, pp. 139-152, 1977.
Olsson et al., "N$^6$-Substituted N-Alkyladenosine-5'-Uronamides: Bifunctional Ligands Having Recognition Groups for A1 and A2 Adenosine Receptors", J. Med. Chem. 1986, vol. 29, pp. 1683-1689.
Collis et al., "Evidence That the Intracellular Effects of Adenosine in the Guinea-Pig Aorta Are Mediated by Inosine", European Journal of Pharmacology, vol. 121, pp. 141-145, 1986.
Jacobson et al., "A Functionalized Congener Approach to Agonists and Antagonists for Adenosine Receptors", Adenosine & Adenine Nucleotides: Physiology and Pharmacology, 1988, pp. 27-38.

(List continued on next page.)

Primary Examiner—Mukund J. Shah
Assistant Examiner—Matthew V. Grumbling
Attorney, Agent, or Firm—Poms, Smith, Lande & Rose

[57] ABSTRACT

Novel bi-functional pharmaceutical compounds, particularly novel 9-substituted hypoxanthines of the general formula:

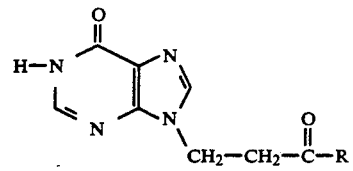

where R is a neurologically active moiety, are described as pharmaceutical agents for treating neuroimmunologic disorders in mammals. Novel methods for the utilization of these compounds are also disclosed. These compounds exhibit uniquely dose-dependent, synergistic biological properties and are particularly useful for treating interrelated physiological systems.

10 Claims, No Drawings

OTHER PUBLICATIONS

Daly et al., "7-Deaza-9-Phenyladenines: A New Class of Adenosine Receptor Antagonists", Biochemical Pharmacology, vol. 37, No. 19, pp. 3749–3753, 1988.

Arthur D. Broom, "Rational Design of Enzyme Inhibitors: Multisubstrate Analogue Inhibitors", American Chemical Society, 1988.

Jacob et al., "Synthesis, Brain Uptake, and Pharmacological Properties of a Glyceryl Lipid Containing GABA and the GABA-T Inhibitor γ-Vinyl-GABA", J. Med. Chem., vol. 33, pp. 733–736, 1990.

Hardy et al., "An Integrative Hypothesis Concerning the Pathogenesis and Progression of Alzheimer's Disease", Neurobiology of Aging, vol. 7, pp. 489–502, 1986.

Singh and Fudenberg, "Implications of Immunomodulant Therapy in Alzheimer's Disease", Progress in Drug Research, vol. 32, pp. 21–42, 1988.

Glasky and Gordon, "Inosiplex Treatment of Acquired Immuno-Deficiencies: A Clinical Model for Effective Immunomodulation", Meth and Find Clin Pharmacol 1986, 8(1):35–40.

Burnett et al., "Dialkylaminoalkanol Esters of p-Aminobenzoic Acid", J. Am. Chem. Soc., vol. 59, pp. 2248–2252, 1937.

5,091,432

9-SUBSTITUTED HYPOXANTHINE BI-FUNCTIONAL COMPOUNDS AND THEIR NEUROIMMUNOLOGICAL METHODS OF USE

FIELD OF THE INVENTION

The present invention is directed to novel multi-functional pharmaceutical compounds possessing unique and unexpected combinations of biological activities. More particularly, the compositions are formed of at least two biologically active chemical moieties linked by a chemical bridge. Each chemical moiety structurally resembles any of a wide variety of biologically active compounds possessing pharmacological activities such as immuno-modulation, neurologic modulation, cardiovascular modulation, anti-microbial activity and other therapeutic properties. The multi-functional compounds express these combinations of pharmacological activities in uniquely dose-dependent and supportive manners enabling previously unavailable therapies and combination therapies to be practiced and regulated through the administration of appropriately effective dosages of individual pharmaceutical compositions.

BACKGROUND OF THE INVENTION

The modification of pharmaceutical and biologically active compounds to alter or enhance their functional properties is known in the art. Typically, prior art efforts have been directed to the production of carrier-bound drugs in which carrier molecules having selective physical properties, such as enhanced water solubility, are chemically attached to biologically active compounds. For example, Jacobson and colleagues have developed what is referred to as the "functional congener" approach to the design of carrier-bound drugs (Jacobson, K. A., in *Adenosine Receptors*; Cooper, D. M. F., Londos, C., Eds, *Receptor Biochemistry and Methodology*; Venter, J. C., Harrison, L. C., Eds., Alan R. Liss: New York, 1988, Vol. 11, pp. 1–26). This approach involved the modification of well defined drug molecules at non-sensitive positions in a manner that retained the drug's ability to bind at its specific receptor site. In order to produce a chemically functionalized drug congener, they modified the drug molecule through the introduction of a chemical functional group which could then be covalently attached to a carrier molecule. This produced a bifunctional molecule in which one portion (the "pharmacophore") contributed its biological activity, and the second portion, or carrier, imparted its selective physical properties such as enhanced receptor attachement or water solubility. Using this approach, functional congener compounds were prepared utilizing catecholamines, adenosine receptor agonists and antagonists, and muscarinic agents.

However, recent developments in the understanding of biological mechanisms such as the binding of selective ligands to receptors and their related functions in such seemingly diverse physiological systems as the cardiovascular system, central nervous system and the immune system have stimulated efforts to discover alternative methods for designing biologically active compounds exhibiting properties which will selectively treat or regulate such seemingly diverse chemical systems without serious or disabling side effects. For example, adenosine receptors have been found in the cardiovascular system, central nervous system and in the immune system. Accordingly, it was originally believed that the development of adenosine analogs would be effective at regulating or modifying the biological activities associated therewith. However, the ubiquitous distribution of adenosine receptors has resulted in the production of serious and disabling side effects in what were originally believed to be unrelated biological systems, thereby significantly reducing the therapeutic usefulness of adenosine analogs.

Similar inter-relationships have also been discovered to exist in the mammalian immune system and nervous system. Over the past several decades numerous researchers have added considerable detail to the overall understanding of the mammalian immune system and its importance in maintaining overall physical health. In more recent years, similar detail has evolved in the study of the nervous system. As more and more information was developed in these seemingly independent fields of study, a number of close functional parallels began to appear between the two physiological systems. For example, both systems are concerned with the storage of information and use soluble chemicals to transmit signals between cells. Additionally, natural endogenous substances, such as hormones and transmitters, are active on the cells of both systems. Even more significantly, some common functions between the two systems are based upon similar chemical structures or markers on the surfaces of both nerve cells and immune cells. The recent discovery that the CD4 receptors targeted by the AIDS virus are present on both the T4 lymphocyte and on neurons is one of the more dramatic examples of the close relationship between the nervous system and the immune system.

Further crossing the classically imposed barriers between the fields of immunology and neurology, recent developments in the understanding of Alzheimer's disease have implicated an immunologic component may be present in this neurological disorder. It has been proposed that both the anatomical and biochemical specificity of the defects seen in Alzheimer's disease could be explained by an immunologic attack on the brain blood vessels themselves with secondary involvement of neuronal, glial, or synaptic constituents contributing to the formation of senile plaques, or an immune-mediated compromise of vessels associated with an immune attack on specific neuronal, glial, or synaptic constituents (Appel, S. H., Neurobiol. Aging, 7:512, 1986).

Additionally, circumstantial evidence for an immunological component in neurologic disorders is also provided by the altered suppressor cell function in aging populations, and more specifically in Alzheimer's disease (MacDonald et al., Clin. Exp. Immunol. 49:123–8, 1982; Miller, A. E., Ann. Neurol. 10: 506–10, 1981; Stefansson, K. in *Clinical Neurology of Aging*, ed. M. L. Albert, Oxford Univ. Press, 1984, pp. 76–94), the implication of HLA regions of chromosome 6 and the GM locus chromosome 14 in a large kindred with Alzheimer's disease (Weitkamp, L.R.m Am. J. Hum. Genet. 35:443–53, 1983), and by the altered immunological parameters in Down's syndrome, a disease whose symptoms are similar to senile dimentia of the Alzheimer's type (SDAT).

Scientists in the nascent field of neuroimmunology have hypothesized that defects in the function of brain cells (neurons) may be observed concomittantly as parallel defects or deficiencies in receptors on the cells of the immune system (such as peripheral blood immune cells). The validity of this hypothesis was recently brought to light with the aforementioned discovery of HIV infection in neurons. This neuroimmunologic theory has had significant impact because formerly almost all neuropsychiatric disorders were thought to be primarily due to factors such as genetic predisposition, mental attitudes, and/or resistance to natural environment rather than defects or deficiencies in cell function. Similarly, though the immune system has been implicated in numerous diseases ranging from infection and cancer to degenerative diseases such as Alzheimer's disease, arthritis and aging, its relationship to cognitive functioning was previously unrealized.

Because the chemical inter-relationship between these diverse physiological systems has been recognized only recently, prior art medical treatments and pharmaceutical agents have focused almost exclusively on treating the individual systems alone. Thus, pharmaceutical compounds have been developed for treating or regulating the cardiovascular system or the immune system or the central nervous system with the idea of avoiding undesirable interactions in what are now known to be related physical systems. By far the greatest amount of recent effort in the pharmaceutical and medical fields has been devoted to the treatment or regulation of the immune system alone. Numerous immunomodulating and antiviral agents have been disclosed in the art such as those described in European Patent Application Publication No. 0 126 813 (Simon, et al.) U.S. Pat. No. 4,221,909 (Simon, et al.), U.S. Pat. No. 4,211,794 (Kraska), and U.S. Pat. No. 4,221,910 (Giner-Sorolla). Unlike antibiotics which directly attack or destroy invading organisms such as bacteria, immunomodulating agents and more specifically immune enhancing agents are compounds which help to bolster the body's own defense mechanisms against the effects of infections. Immunomodulators either restore depressed immune function, or suppress hyperactive immune function.

Though the AIDS epidemic has focused considerable resources and attention to the study of defects and deficiencies in the immune system, outside of the recent discovery of HIV infection in neural tissue, comparatively little research has been directed to the development of multi-functional pharmaceutical compounds such as neuroimmunologic agents or other compounds exhibiting functionally related and mutually supportive therapeutic activies such as immuno-modulating with cardiovascularly active compounds or immuno-modulating with anti-microbially active compounds.

Accordingly, it is a principal object of the present invention to disclose multifunctional pharmaceutical compounds possessing at least two separate pharmacological activities that are functionally related and mutually supportive therapeutically.

It is an additional object of the present invention to provide multi-functional pharmaceutical compounds pairing biologically active chemical moieties such as immuno-modulating pharmacophores, neurological pharmacophores, cardiovascular pharmacophores, and anti-microbial pharmacophores as well as others.

It is a further additional object of the present invention to provide multi-functional pharmaceutical compounds combining biologically active chemical moieties which produce a combined pharmacological activity differing in either or both quantity or character from the individual pharmacological activities of the separate chemical moieties.

It is a further additional object of the present invention to disclose specific neurologically active immuno-modulating compounds that are pharmaceutically active with respect to defects or deficiencies common to both the central nervous system and to the immune system. These particular compounds will be especially effective for treating neuroimmunologic conditions such as Alzheimer's disease, AIDS, memory and immune function, as well as the effects of aging.

SUMMARY OF THE INVENTION

These and other objects are achieved by the multi-functional pharmaceutical compositions of the present invention which combine at least two biologically active chemical moieties linked by at least one chemical bridging group. The coupled chemical moieties can be any pharmacologically relevant combination of biologically active molecules possessing separate pharmacological activities. For example, in accordance with the teachings of the present invention, it is possible to produce biologically active compounds pairing immuno-modulating moieties with neurological moieties. Similarly, other pairings are possible within the scope of the present invention, such as combining moieties having cardiovascular activity with chemical moieties possessing anti-microbial activities and the like.

Preferably, the multi-functional pharmaceutical compounds of the present invention will be formed of distinct biologically active chemical moieties linked by chemical bridging groups such as propionic acid, butyric acid or derivatives thereof. Chemical bridging groups that are biogradeable such as amide or peptide linkages are preferred as it is believed that such bridging groups will be readily hydrolyzed by known proteolytic enzymes enabling the individual chemical structural moieties to function independently if desired. However, it should be emphasized at this point that the individual chemical moieties may remain interlinked and thus simultaneously interact with adjacent or structually close receptor sites on treated cells and remain within the teachings of the present invention.

The multi-functional compounds of the present invention may be formulated into novel pharmaceutical compositions incorporating effective concentrations of the specific compounds and pharmaceutically acceptable carriers. These pharmaceutical compositions may then be utilized to practice methods of treatment within the scope of the present invention wherein effective amounts of the pharmaceutical compositions so produced are administered orally or by injection to mammalian patients suffering from conditions such as Alzheimer's disease, neuroimmunologic disorders, neuro-cardiovascular disorders, and the like.

Further objects and advantages of the multi-functional pharmaceutical compounds of the present invention, as well as a better understanding thereof, will be afforded to those skilled in the art from a consideration of the following detailed explanation of preferred exemplary embodiments thereof.

DETAILED DESCRIPTION OF EXEMPLARY EMBODIMENTS

In a broad aspect, the multi-functional pharmaceutical compounds of the present invention are formed from at least two biological active chemical moieties linked by at least one chemical bridging group. Each of the chemical moieties or pharmacophores contributes its own biological activity to the properties of the multifunctional compound. Preferably, these biological activities will include immunologic or immuno-modulating activity, neurological activity, cardiovascular activity, or anti-microbial activity through other combinations of biological activities are contemplated as being within the scope of the present invention. For example, each of the chemical moieties can be formed from the active chemical structural core of a specific type of biologically active molecule, or, alternatively, from selective drug congeners or other biologically active compounds. Thus, unlike the prior art carrier-bound drugs, the compounds of the present invention are formed of multiple biologically active pharmacophores which may also function as carriers in addition to their respective biological activities. More significantly, it was surprisingly discovered that the compounds of the present invention exhibit unique pharmacological activities differing in quantity, character or both from the individual activities of the respective pharmacophores.

In accordance with the teaching of the present invention, it is preferred that the individual pharmacophores be covalently linked by a chemical bridging group. Preferably, the bridging group will contain biodegradeable linkages such as single or multi-amide or peptide-like linkages. In this manner, it is possible for the chemical structural moieties of the compounds of the present invention to function independently following hydrolyzation of the chemical bridging group. Exemplary bridging groups in accordance with the teachings of the present invention are propionic acid and butyric acid or derivatives thereof such as propanamide. Though it was believed that such biodegradeable linkages would be hydrolyzed by known proteolytic enzymes present in the body to allow such independent function to occur, in view of the completely unexpected biological activities observed for these compounds, it is now proposed that the respective chemical moieties of each compound may remain linked. As a result, it is believed that these linked, biologically active chemical moieties are able to simultaneously interact with adjacent or structurally close receptor sites on individual cells. More particularly, the uniquely dose-dependent activities, synergistic biological properties, and diverse specific biological effects of the compounds of the present invention are indicative of unusual and unexpected interactive mechanisms which cannot be explained by simple biodegradation of the chemical linking group.

Exemplary pharmacophores for practicing the present invention can be selected from those chemical moieties exhibiting biological activity in the following therapeutic classes: analgesic, anthelminthic, anti-ulcer, antibacterial, antibiotic, anticonvulsant, antifungal, antihypertension, antimalarial, antineoplastic, arthritis, bronchodilator, cardiovascular, immunologic, depression, diuretic, diuretic-carbonic anhydrase inhibitor, muscle relaxant, neurologic, neurotransmitter, Parkinsonism, psychostimulant and sympathomimetic. However, those skilled in the art will appreciate that other therapeutic classes of pharmacophores are contemplated as being within the scope of the present invention.

Thus, the multi-functional pharmaceutical compounds of the present invention can be formed from chemically bridged combinations of moieties such as aspirin, piperazine, clmetidine, ranitidine, sulfamethoxazole, sulfisoxazole, penicillin G, cephalosporin C, tetracycline, phenytoin, flucytosine, aminobutyric acid, primaquine, pyrimethamine, methostrexate, naproxen, ibufren, epinephrine, ephedrine, theophylline, captopril, acebutol, flecainide, mexiletine, procainamide, tocainide, carnitine, chlordiazepoxide, desipramine, maprotiline, meprobamate, nortriptyline, protriptyline, tranylcypromine, amiloride, triamterene, ethacrynic acid, acetazolamide, captopril, prazosin, baclofen, hypoxanthine, 5-hydroxytryptamine, levodopa, methamphetamine, methylphenidate, pemoline, dextroamphetamine, dopamine, or structurally similar biologically active compounds.

Though within the scope of the present invention to combine chemical moieties having widely diverse biological activities including immunological, neurological, cardiovascular and anti-microbial properties, the following exemplary embodiments of the present invention are formed of linked immuno-modulating pharmacophores and neurological pharmacophores. As noted above, the rationale for coupling biologically active chemical compounds having immunological and neurological activities is based upon the functional relationship between the central nervous system and the immune system due to the presence of similar, relevant surface markers being present on the cells of each system. Additionally, defects in the function of brain cells have been observed concomittantly with defects in the function of peripheral blood immune cells.

Accordingly, in accordance with the teachings of the present invention, it is particularly desirable to produce compounds that are designed to correct functional defects in both immune and nerve cells. As those skilled in the art will appreciate, because specific neurological and immune defects or deficiencies are known in both Alzheimer's disease and in conjunction with the neurological aspects of HIV infection, these syndromes or conditions are principal targets of the exemplary embodiments of the present invention. Similarly, the diseases of schizophrenia and the neuroimmunological deficiencies associated with aging are also targets of these embodiments. It should be emphasized that the following, non-limiting examples are illustrative of the present invention and are in no way intended to limit the scope of the present invention to neuroimmunologic compounds.

Exemplary multi-functional pharmaceutical compounds exhibiting neuroimmunological properties in accordance with the teachings of the present invention can be formed from a first biologically active chemical moiety having immunological activity and a second biologically active chemical moiety having neurological activity. An exemplary immunological chemical moiety is hypoxanthine or purin-6(1H)-one, for purposes of explanation herein identified as AIT-001. An additional benefit to the utilization of hypoxanthine in the compounds of the present invention is its structural relationship to inosine, the only purine known to cross the blood-brain barrier. Thus, in addition to its biological activity as an immunological compound, hypoxanthine may also function as a carrier or targeting portion of the molecule that will deliver the multi-function pharmaceutical compound to particular targeted organs such as the brain. In accordance with the teachings of the present invention, hypoxanthine is linked by a chemical bridging group such as propionic acid or butyric acid to a wide variety of neurologically active chemical moieties to produce the following exemplary compounds (structural formulas for which are provided in Appendix A):

AIT COMPOUNDS

AIT-0026
3-(6-amino-9H-purin-9-yl)propionic acid, ethyl ester
AIT-0027
3-(1,6-dihydro-6-oxo-9H-purin-9-yl)propionic acid, ethyl ester
AIT-0029
3-(1,6-dihydro-6-oxo-9H-purin-9-yl)-N-[(1-ethyl-pyrrolidin-2-yl)methyl]propanamide
AIT-0031
3-(1,6-dihydro-6-oxo-9H-purin-9-yl)-N-[2-(4-morpholinyl)ethyl]propanamide
AIT-0033
3-(1,6-dihydro-6-oxo-9H-purin-9-yl)-N-(1-benzyl-piperidin-4-yl)propanamide
AIT-0034
3-(1,6-dihydro-6-oxo-9H-purin-9-yl)-N-[3-(2-oxopyrolidin-1-yl)propyl]propanamide
AIT-0035
3-(1,6-dihydro-6-oxo-9H-purin-9-yl)-N-[2-(1-methyl-pyrrol-2-yl)ethyl]propanamide
AIT-0037
3-(1,6-dihydro-6-oxo-9H-purin-9-yl)-N-[3-(1-imidazolyl)propyl]propanamide
AIT-0043
3-(1,6-dihydro-6-oxo-9H-purin-9-yl)-N-[3-(4-morpholinyl)propyl]propanamide
AIT-0044
3-(1,6-dihydro-6-oxo-9H-purin-9-yl)-N-[3-(2-methyl-piperidin-1-yl)propyl]propanamide
AIT-0045
3-(1,6-dihydro-6-oxo-9H-purin-9-yl)-N-[2-(1-methyl-pyrrolidin-2-yl)ethyl]propanamide
AIT-0046
3-(1,6-dihydro-6-oxo-9H-purin-9-yl)-N-(2-hydroxyethyl)propanamide
AIT-0047
3-(1,6-dihydro-6-oxo-9H-purin-9-yl)-N-[2-(2-hydroxyethoxy)ethyl]propanamide
AIT-0048
3-(1,6-dihydro-6-oxo-9H-purin-9-yl)-N-[2-[(2-hydroxyethyl)amino]ethyl]propanamide
AIT-0049
3-(1,6-dihydro-6-oxo-9H-purin-9-yl)-N-[2-(4-aminosulfonylphenyl)ethyl]propanamide
AIT-0050
3-(1,6-dihydro-6-oxo-9H-purin-9-yl)-N-[(2-hydroxy-1-methyl-2-phenyl)ethyl]propanamide
AIT-0051
3-(1,6-dihydro-6-oxo-9H-purin-9-yl)-N-[2-[(1-oxoethyl)amino]ethyl]propanamide
AIT-0052
3(1,6-dihydro-6-oxo-9H-purin-9-yl)-1-[1,4-dioxa-8-azaspiro[4.5]dec-8-yl]]propanone
AIT-0056
3-(1,6-dihydro-6-oxo-9H-purin-9-yl)propanoic acid hydrazide
AIT-0058
3-(1,6-dihydro-6-oxo-9H-purin-9-yl)-N-(2-aminoethyl)propanamide
AIT-0059
3-(1,6-dihydro-6-oxo-9H-purin-9-yl)-N-(2-hydroxypropyl)propanamide
AIT-0060
3-(1,6-dihydro-6-oxo-9H-purin-9-yl)-N-[(2-furanyl)methyl)]propanamide
AIT-0062
3-(1,6-dihydro-6-oxo-9H-purin-9-yl)-N-(2,3-dihydroxy-prop-1-yl)propanamide
AIT-0063
3-(1,6-dihydro-6-oxo-9H-purin-9-yl)-N-[(2-pyridinyl)methyl]propanamide
AIT-0064
3-(1,6-dihydro-6-oxo-9H-purin-9-yl)-N-[2-(diethylamino)ethyl]propanamide
AIT-0065
3-(1,6-dihydro-6-oxo-9H-purin-9-yl)-N-[2-[[2-(2-oxopyrrolidin-1-yl)-1-oxoethyl]-amino]ethyl]propanamide
AIT-0066
3-(1,6-dihydro-6-oxo-9H-purin-9-yl)-N-piperonyl-propanamide
AIT-0068
3-(1,6-dihydro-6-oxo-9H-purin-9-yl)-N-[2-(1-pyrrolidinyl)ethyl]propanamide
AIT-0069
N,N',N''-tri[2-[3-(1,6-dihydro-6-oxo-9H-purin-9-yl)-1-oxopropyl]aminoethyl]amine
AIT-0070
3-(1,6-dihydro-6-oxo-9H-purin-9-yl)-N-[[2-(1-piperidinyl)]ethyl]propanamide
AIT-0071
3-(1,6-dihydro-6-oxo-9H-purin-9-yl)-N-[2-(2,2'-diethanolamino)ethyl]propanamide
AIT-0072
3-(1,6-dihydro-6-oxo-9H-purin-9-yl)-N-[2-(1H-indol-3-yl)ethyl]propanamide
AIT-0073
2-[6-amino-9H-purin-9-yl)methyl]butanedioic acid, methyl diester
AIT-0074
3-(1,6-dihydro-6-oxo-9H-purin-9-yl)-N-(3-aminopropyl)propanamide
AIT-0075
2-[(1,6-dihydro-6-oxo-9H-purin-9-yl)methyl]-butanedioic acid, methyl diester
AIT-0079
4-[[3-(1,6-dihydro-6-oxo-9H-purin-9-yl)-1-oxopropyl]amino]benzoic acid, ethyl ester
AIT-0080
3-(1,6-dihydro-6-oxo-9H-purin-9-yl)propanoic acid
AIT-0081
3-(1,6-dihydro-6-oxo-9H-purin-9-yl)propanoic acid, 4-nitrophenyl ester
AIT-0082
4-[[3-(1,6-dihydro-6-oxo-9H-purin-9-yl)-1-oxopropyl]amino]benzoic acid
AIT-0083
4-[[3-(1,6-dihydro-6-oxo-9H-purin-9-yl)-1-oxopropyl]amino]benzoic acid compd with 1-(dimethylamino)-2-propanol (1:1)
AIT-0084
4-[[3-(1,6-dihydro-6-oxo-9H-purin-9-yl)-1-oxopropyl]amino]benzoic acid, 1-(dimethylamino)-2-propyl ester
AIT-0085
2-[[3-(1,6-dihydro-6-oxo-9H-purin-9-yl)-1-oxopropyl]amino]-3-phenylpropanoic acid, methyl ester
AIT-0086
2-[[3-(1,6-dihydro-6-oxo-9H-purin-9-yl)-1-oxopropyl]amino]-3-phenylpropanoic acid
AIT-0087
3-(1,6-dihydro-6-oxo-9H-purin-9-yl)-N-[2-(2-deoxyglucopyranosyl)]propanamide
AIT-0090

4-[[2-[[3-(1,6-dihydro-6-oxo-9H-purin-9-yl)-1-oxo-propyl]amino]ethyl]amino]-2-hydroxy-4-oxo-N,N,N-trimethyl-1-butanaminium chloride
AIT-0092

4-[[3-(1,6-dihydro-6-oxo-9H-purin-9-yl)-1-oxopropyl]amino]butanoic acid, methyl ester
AIT-0093

3-[[3-(1,6-dihydro-6-oxo-9H-purin-9-yl)-1-oxopropyl]amino]propane sulfonic acid
AIT-0094

1-[2-[[3-(1,6-dihydro-6-oxo-9H-purin-9-yl)-1-oxo-propyl]hydrazino]2-oxoethyl]pyridinium chloride
AIT-0095

4-[[3-(1,6-dihydro-6-ox-9H-purin-9-yl)-1-oxopropyl]amino]-N-[2-(diethylamino)ethyl]benzamide monohydrochloride
AIT-0096

3-(1,6-dihydro-6-oxo-9H-purin-9-yl)-N-(2-oxothiaolan-3-yl)propanamide
AIT-0097

3-(1,6-dihydro-6-oxo-9H-purin-9-yl)-N-[2-(3,4-dihydroxyphenyl)-2-hydroxyethyl]propanamide
AIT-0098

3-(1,6-dihydro-6-oxo-9H-purin-9-yl)-1-(1-phenyl-4-oxo-1,3,8-triazaspiro[4.5]dec-8-yl)-propanone
AIT-0099

3-(1,6-dihydro-6-oxo-9H-purin-9-yl)-1-(1,2,3,4-tetrahydro-2-azacarbazo-2-yl)propanone
AIT-0100

3-(1,6-dihydro-6-oxo-9H-purin-9-yl)-N-[2-(3,4-dihydroxyphenyl)-2-hydroxyethyl]-N-methylpropanamide
AIT-0102

3-(1,6-dihydro-6-oxo-9H-purin-9-yl)-1-(2-phenylimidazo-1-yl)propanone
AIT-0103

1-[3-(1,6-dihydro-6-oxo-9H-purin-9-yl)-1-oxopropyl]-3-piperidinecarboxyliacid ethyl ester
AIT-0105

4-[[3-(1,6-dihydro-6-oxo-9H-purin-9-yl)-1-oxopropyl]amino]benzoic acid, 1-(dimethylamino)-2-propyl ester, monohydrochloride
AIT-0106

3-(1,6-dihydro-6-oxo-9H-purin-9-yl)propanoic acid, 1-(dimethylamino)-2-propyl ester
AIT-110

3-(1,6-dihydro-6-oxo-9H-purin-9-yl)propanoic acid, compd with 1-(dimethylamino)-2-propanol (1:1)
AIT-0111

2-[[3-(1,6-dihydro-6-oxo-9H-purin-9-yl)-1-oxopropyl]amino]-2-(5-hydroxyl-1H-indol-3-yl)-propionic acid These exemplary neuroimmunologic multi-function pharmaceutical compounds can be prepared as described in the following non-limiting examples.

EXAMPLE 1

Synthesis of
3-(1,6-dihydro-6-amino-9H-purin-9-yl)propionic acid, ethyl ester (AIT-0026)

Adenine (10.00 g., 74.00 mmol) was placed into a clean, dry 500 ml round bottom flask equipped with a magnetic stirring bar, reflux condenser, and a CaCl$_2$ drying tube. Absolute ethanol (360 ml) was added and the solution was stirred. To the suspension was added a small piece of Sodium (approximately 75 mg). When the Sodium had completely reacted, 22.2 g (0.222 mol) ethyl acrylate was added to the suspension and the mixture was brought to reflux. Reflux was continued overnight for approximately 18 hours and the resulting lime colored homogeneous solution was allowed to cool slowly to room temperature. Crystals were allowed to form at 4° C. The solution was filtered by Buchner vacuum filtration and the solid was washed with anhydrous ether. Upon drying, 15.2 g (64.6 mmol) of 3-(1,6-dihydro-6-amino-9H-purin-9-yl)propionic acid, ethyl ester (AIT-0026) was obtained. Yield: 87%.
mp: 166°–167° C.

EXAMPLE 2

Synthesis of
3-(1,6-dihydro-6-oxo-9H-purin-9-yl)propionic acid, ethyl ester (AIT-0027)

3-(1.6-dihydro-6-amino-9H-purin-9-yl)propionic acid, ethyl ester (15.2 g., 64.6 mmol) (AIT-0026) was placed into a 500 ml round bottom flask with 350 ml glacial acetic acid and was stirred to complete dissolution. While stirring, 22.3 g (0.323 mol) NaNO$_2$ dissolved in water (saturated) was added dropwise over a period of one hour using a dropping funnel (pressure equalizing). A brown gas formed during the addition. The flask was stoppered shortly after the addition was complete and the solution was stirred at room temperature for 24 hours. The solvent was removed under reduced pressure (approximately 45°–50° C.). The residue was washed with cold (0° C.) absolute ethanol and filtered. The resulting white solid was dissolved in 175 ml ethanol/water (70/30) and was cooled to 0° C. overnight. The resulting precipitate was obtained by filtration. The solid was placed into a flask with a magnetic stirring bar and was washed with water by vigorous stirring. The solution was filtered by Buchner vacuum filtration and the resulting white solid was dried in vacuo at 50° C. to yield 4.6 g (19.5 mmol) of 3-(1,6-dihydro-6-oxo-9H-purin-9-yl)propionic acid, ethyl ester (AIT-0027). Yield: 30%.
mp: 197°–200° C.

EXAMPLE 3

Synthesis of
3-(1.6-dihydro-6-oxo-9H-purin-9-yl)-N-[(1-ethylpyrrolidin-2-yl)methyl]propanamide (AIT-0029)

3-(1.6-dihydro-6-oxo-9H-purin-9-yl)propionic acid, ethyl ester (250 mg. 1.06 mol) (AIT-0027) was placed into a 10 ml round bottom flask equipped with a magnetic stirring bar, reflux condenser and CaCl$_2$ drying tube. Then 3 ml acetonitrile and 280 mg (2.18 mmol) 2-(aminomethyl)-1-ethyl-pyrrolidine were added and the solution was heated to reflux. Not all of the ester dissolved at reflux, but as the reaction proceeded, the solution became homogeneous. Reflux was continued for 17 hours, at which time the solvent had completely evaporated. The residue was treated with acetonitrile and allowed to cool. A white precipitate had formed. Ether was added and the solution was stirred to wash the precipitate. The solution was filtered by Buchner vacuum filtration and the precipitate was washed with ether. Upon drying, 300 mg (0.94 mmol) of 3-(1,6-dihydro-6-oxo-9H-purin-9-yl)-N-[(1-ethyl-2-pyrrolidinyl)-methyl]propanamide (AIT-0029) was obtained as an off-white solid.
mp: 177°–180° C.

EXAMPLE 4

Synthesis of
3-(1,6-dihydro-6-oxo-9H-purin-9-yl)-N-[2-(4-morpholinyl)ethyl]propanamide (AIT-0031)

250 mg (1.06 mmol) of 3-1,6-dihydro-6-oxo-9H-purin-9-yl) propionic acid, ethyl ester (AIT-0027) was placed into a 10 ml round bottom flask with a magnetic stirring bar, reflux condenser, a $CaCl_2$ drying tube and 3 ml acetonitrile. Then, 280 mg (2.15 mmol) 4-(2-aminoethyl)-morpholine was added. The solution was then brought to reflux. Reflux was continued for 18 hours. An additional 280 mg (2.15 mmol) of 4-(2-aminoethyl)-morpholine was added, some of the acetonitrile was evaporated to give a more concentrated solution, and the solution was again brought to reflux for 28 hours. Some acetonitrile (4 ml) was added to the dark viscous residue and the solution was stirred. A white precipitate had formed and this was collected by buchner filtration. The solid was washed with acetonitrile and then with ether. Upon drying, 250 mg of 3-(1,6-dihydro-6-oxo-9H-purin-9-yl)-N-[2-(4-morpholinyl) ethyl] propanamide (AIT-0031) was obtained as a slightly off-white solid. Yield: 74%.

EXAMPLE 5

Synthesis of
3-(1,6-dihydro-6-oxo-9H-purin-9-yl)-N-(1-benzylpiperidin-4-yl)propanamide (AIT-0033)

250 mg. (1.06 mmol) 3-(1,6-dihydro-6-oxo-9H-purin-9-yl) propionic acid, ethyl ester (AIT-0027) was added to a 10 ml round bottom flask equipped with a magnetic stirring bar, reflux condenser and $CaCl_2$ drying tube. Then, 604 mg (3.17 mmol) 4-amino-1-benzyl-piperidine and 1 ml acetonitrile were added and the solution was brought to reflux. Reflux was continued for 17 hours. Aacetonitrile was evaporated and the mixture was heated at 120° C. for eight hours to yield a dark viscous oil. The oil was treated with ether while stirring. The solution was filtered and the orangebrown solid was washed with additional ether. Upon drying, 385 mg of a brown solid was obtained. The solid was stirred in acetone, filtered, washed with acetone and then with ether. This yielded 200 mg of 3-(1,6-dihydro-6-oxo-9H-purin-9-yl)-N-(1-benzylpiperidin-4-yl)propanamide (AIT-0033) as a tan solid. Analysis by HPLC indicated that the product was 65% pure.

EXAMPLE 6

Synthesis of
3-(1,6-dihydro-6-oxo-9H-purin-9-yl)-N-[3-(2-oxopyrrolidin-1-yl) propyl]propanamide (AIT-0034)

250 mg (1.06 mmol) of 3-(1,6-dihydro-6-oxo-9H-purin-9-yl)propionic acid, ethyl ester (AIT-0027) was added to a 10 ml round bottom flask equipped with a magnetic stirring bar, reflux condenser, and a $CaCL_2$ drying tube. 452 mg (3.18 mmol) 1-(3-aminopropyl)-2-pyrrolidinone and 1 ml acetonitrile were added. The solution was heated to reflux for 17 hours at which time all of the acetonitrile was evaporated leaving a dark viscous oil. The oil was chromatographed on 15 g silica gel, eluting with 40% methanol/60% ethyl acetate. This procedure gave 185 mg of 3-(1,6-dihydro-6-oxo-9H-purin-9-yl)-N-[3-(2-oxopyrrolidin-1-yl)propyl]-propanamide (AIT-0034) as a pure white solid. Yield: 53%

EXAMPLE 7

Synthesis of
3-(1,6-dihydro-6-oxo-9H-purin-9-yl)-N-[2-(1-methylpyrrol-2-yl)ethyl] propanamide (AIT-0035).

250 mg (1.06 mmol) of 3-(1,6-dihydro-6-oxo-9H-purin-9-yl)propionic acid, ethyl ester (Alt-0027) and 400 mg (3.22 mmol) of 2-(2-aminoethyl)-1-methyl-pyrrole were heated together in a 10 ml round bottom flask with stirring (no solvent) at 110°–120° C. for 3.5 hours. The dark viscous residue was treated with a 1:1 mixture of ether/acetone and stirred vigorously for 30 minutes. The precipitate was collected by filtration and was washed with ether and acetone and dried in vacuo to yield 265 mg of 3-(1,6-dihydro-6-oxo-9H-purin-9-yl)-N-[2-(1-methylpyrrol-2-yl)ethyl] propanamide (AIT-0035) as an off-white solid. Yield: 80%

EXAMPLE 8

Synthesis of
3-(1,6-dihydro-6oxo-9H-purin-9-yl)-N-[3-(1-imidazolyl)propyl]propanamide (AIT-0037)

250 mg (1.06 mmol) of 3-(1,6-dihydro-6-oxo-9H-purin-9-yl) propionic acid, ethyl ester (AIT-0027) was heated with 500 mg (3.99 mmol) of 1-(3-aminopropyl)-imidazole in a 10 ml round bottom flask at 120° C. for two hours with stirring. The resulting viscous yellow oil was chromatographed on 15 g of silica gel, eluting with 60% methanol/40% ethyl acetate, which yielded a highly viscous colorless oil after evaporation of the solvent. The oil was dissolved in approximately 50 ml of ethyl ether and then methanol was added slowly until a white precipitate formed. The precipitate was collected by vacuum filtration and washed with ethyl ether. The material was dried to yield 200 mg of 3-(1,6-dihydro-6-oxo-9H-purin-9-yl)-N-[3-(1-imidazolyl)propyl]propanamide (AIT-0037) as a white solid. Yield 66%.

EXAMPLE 9

Synthesis of
3-(1,6-dihydro-6-oxo-9H-purin-9-yl)-N-[3-(4-morpholinyl)propyl]propanamide (AIT-0043)

475 mg (3.29 mmol) of 4-(3-aminopropyl)morpholine was added to a 10 ml round bottom flask equipped with a magnetic stirring bar. The flask was heated to 100°–120° C. and 250 mg (1,06 mmol) of 3-(1,6-dihydro-6-oxo-9H-purin-9-yl)propionic acid, ethyl ester AIT-0027 was added to the stirring flask. Heating was continued for two hours. The solution was allowed to cool to room temperature and was then treated with 8 ml acetonitrile with stirring. A white precipitate formed and the solution was filtered after 20 minutes of stirring in acetonitrile. The filtrate was washed with acetonitrile and then with ether. This yielded 130 mg of a white solid. The mother liquor was allowed to stand overnight in a fume hood and was filtered the next day to yield another 100 mg of 3-(1,6-dihydro-6-oxo-9H-purin-9-yl)-N-[3-(4-morpholinyl)propyl]propanamide (AIT-0043). Yield: 65%. m.p. 145°–148° C.

EXAMPLE 10

Synthesis of
3-(1,6-dihydro-6-oxo-9H-purin-9-yl)-N-[3-(2-methylpiperidin-1-yl)propyl]propanamide (AIT-0044)

0.565 g (3.62 mmol) of 1-(3-aminopropyl)-2-pipecoline was placed into a 10 ml round bottom flask with a magnetic stirring bar. The flask was heated to 120° C. and 250 mg (1.06 mmol) of 3-(1,6-dihydro-6-oxo-9H-purin-9-yl)propionic acid, ethyl ester (AIT-0027) was added. The mixture was heated for two hours at 120° C. and was allowed to cool. The resultant light orange viscous oil was treated with 8 ml acetonitrile and was stirred for about 25 min. The solution was filtered and the solid was washed with acetonitrile and then with ether. This yielded 254 mg of 3-(1,6-dihydro-6-oxo-9H-purin-9-yl)-N-[3-(2-methylpipiridin-1-yl)propyl]-propanamide (AIT-0044) as an off-white solid.

EXAMPLE 11

Synthesis of 3-(1,6-dihydro-6-oxo-9H-purin-9-yl)-N-[2-(1-methyl-pyrrolidin-2-yl)ethyl]propanamide (AIT-0045)

0.565 g (4.41 mmol) of 2-(2-aminoethyl)-1-methylpyrrolidine was added to a 10 ml round bottom flask equipped with a magnetic stirring bar. The solution was heated and 0.250 g (1.06 mmol) of 3-(1,6-dihydro-6-oxo-9H-purin-9-yl)propionic acid, ethyl ester (AIT-0027) was added and the solution was heated at 110°–120° C. for two hours. The orange solution was allowed to cool to room temperature and 8 ml acetonitrile was added and the solution was stirred for 20 minutes to wash the solid. The solution was filtered by Buchner vacuum filtration and the solid was washed with acetonitrile and then with ether. Upon drying 265 mg of 3-(1,6-dihydro-6-oxo-9H-purin-9-yl)-N-[2-(1-methylpyrrolidin-2-yl)ethyl]propanamide (AIT-0045) as a white solid was obtained.

EXAMPLE 12

Synthesis of 3-(1,6-dihydro-6-oxo-9H-purin-9-yl)-N-(2-hydroxyethyl)propanamide (AIT-0046)

0.500 g. (8.19 mmol) of ethanolamine was placed into a 10 ml round bottom flask with a magnetic stirring bar. The flask was heated and 0.250 g (1.06 mmol) of 3-(1,6-dihydro-6-oxo-9H-purin-9-yl)propionic acid,ethyl ester (AIT-0027) was added to the stirring solution. The solution was heated at 120° C. for one hour. The solution was allowed to cool to room temperature and 8 ml acetonitrile was added. Upon continued stirring, a white precipitate formed. The solution was filtered and the solid was washed with acetonitrile and then with ether. The solid was dried at 100° C. under reduced pressure to yield 240 mg of 3-(1,6-dihydro-6-oxo-9H-purin-9-yl)-N-(2-hydroxyethyl)propanamide (AIT-0046) as a white solid. Yield: 90%. m.p.=225°–229° C.

EXAMPLE 13

Synthesis of 3-(1,6-dihydro-6-oxo-9H-purin-9-yl)-N-[2-(2-hydroxyethoxy)ethyl]propanamide (AIT-047)

0.500 g (4.76 mmol) of 2-(2-aminoethoxy)ethanol was heated with 0.250 g (1.06 mmol) of 3-(1,6-dihydro-6-oxo-9H-purin-9-yl)propionic acid, ethyl ester (AIT-0027) in a 10 ml round bottom flask at 120° C. for one hour. The solution was treated with 8 ml of acetonitrile and stirred vigorously for 20 minutes. The white precipitate was obtained by filtration and was washed with acetonitrile and then with ether. Upon drying, 265 mg of 3-(1,6-dihydro-6-oxo-9H-purin-9-yl)-N-[2-(2-hydroxyethoxy)ethyl]propanamide (AIT-047) as a white solid was obtained. Yield: 85%.

EXAMPLE 14

Synthesis of 3-(1,6-dihydro-6-oxo-9H-purin-9-yl)-N-[2-[(2-hydroxyethyl)amino] ethyl]propanamide (AIT-0048)

0.500 (4,80 mmol) 2-(2-aminoethylamino)ethanol and 0.250 g (1.06 mmol) of 3-(1,6-dihydro-6-oxo-9H-purin-9-yl)propionic acid, ethyl ester (AIT-0027) were heated at 120° C. with stirring in a 10 ml round bottom flask for one hour. The reaction mixture was chromatographed on a 15 g silica-gel column using an eluant of 60% methanol/40% ethyl acetate. After 200 ml of solvent had passed through column, the eluant was changed to 80% methanol/20% ethyl acetate and finally to 100% methanol. The fractions containing the product were combined and evaporated to yield a colorless oil. The oil was treated with 50 ml ether and 5 ml methanol and was agitated with a spatula. The oil was allowed to stand overnight and the resulting white solid was obtained by filtration (120 mg). The solid was washed with ether and was found to be somewhat hygroscopic. Yield: 38%.

EXAMPLE 15

Synthesis of 3-(1,6-dihydro-6-oxo-9H-purin-9-yl)-N-[2-(4-aminosulfonylphenyl)ethyl]-propanamide (AIT-0049)

0.500 g (2.50 mmol) of 4-(2-aminoethyl)benzenesulfonamide was placed into a 10 ml round bottom flask. The flask was heated until the solid had melted. The temperature was adjusted to 150° C. and 250 mg (1.06 mmol) of 3-(1,6-dihydro-6-oxo-9H-purin-9-yl)propionic acid, ethyl ester (AIT-0027) was added and the mixture was heated for one hour with stirring. At this time, 10 ml acetonitrile was added and the solid material was broken up with the aid of a spatula while being stirred. Stirring was continued until there were no more lumps (refluxing acetonitrile). The hot acetonitrile solution was quickly filtered by vacuum and the white solid was washed with acetonitrile and then with ether. This yielded 280 mg of 3-(1,6-dihydro-6-oxo-9H-purin-9-yl)-N-[2-(4-aminosulfonylphenyl)ethyl]propanamide (AIT-0049) as a white solid. Yield: 68%. m.p. 212°–216° C.

EXAMPLE 16

Synthesis of 3-(1,6-dihydro-6-oxo-9H-purin-9-yl)-N-[(2-hydroxy-1-methyl-2-phenyl)ethyl]-propanamide (AIT-0050)

0.535 g (3.54 mmol) of (1S, 2R)-(+) -norephedrine was placed into a 10 ml round bottom flask. The flask was heated to 120° C. and 250 mg (1.06 mmol) of 3-(1,6-dihydro-6-oxo-9H-purin-9-yl)propionic acid, ethyl ester (AIT-0027) was added to the melted norephedrine with stirring. The reaction was complete after 4.25 hours. 8 ml acetonitrile was added to the solid mass and was broken up with a spatula. The solution was stirred for 45 minutes and was filtered by suction. The white solid was washed with acetonitrile and then with ether. Upon drying, 210 mg of 3-(1,6-dihydro-6-oxo-9H-purin-9-yl)-N-[(2-hydroxy-1-methyl-2-phenyl)ethyl]propanamide (AIT-0050) as a white solid was obtained. Yield: 58%. m.p. 210°–215° C.

EXAMPLE 17
Synthesis of
3-(1,6-dihydro-6-oxo-9H-purin-9-yl)-N-[2-[(1-oxoethyl)amino]ethyl]propanamide (AIT-0051)

0.516 g (5.05 mmol) of N-acetylethylenediamine was placed into a 10 ml round bottom flask. The flask was heated to 120° C. and 0.250 g (1.06 mmol) of 3-(1,6-dihydro-6-oxo-9H-purin-9-yl)propionic acid, ethyl ester (AIT-0027) was added to the stirring solution. The solution was heated at 120° C. for one hour. 8 ml of acetonitrile was added to the viscous oil and stirred. Approximately 1 ml of methanol was added and the solution was stirred vigorously for 30 minutes. The resulting white precipitate was collected by vacuum filtration and was washed with acetonitrile and ether to yield 237 mg of 3-(1,6-dihydro-6-oxo-9H-purin-9-yl)-N-[2-[(1-oxoethyl)amino]ethyl]propanamide (AIT-0051) as a white solid upon drying. Yield: 76%

EXAMPLE 18
Synthesis of
3-(1,6-dihydro-6-oxo-9H-purin-9-yl)-1-[1,4-dioxa-8-azaspiro[4.5]dec-8-yl]propanone (AIT-0052)

0.500 (3.49 mmol) of 1,4-dioxa-8-azaspiro [4.5] decane was placed into a 10 ml round bottom flask with a magnetic stirring bar. The amine was heated to 110° C. and 0.250 g (1.06 mmol) of 3-(1,6-dihydro-6-oxo-9H-purin-9-yl)propionic acid, ethyl ester (AIT-0027) was added and the solution was heated for four hours. The reaction was stopped, 10 ml acetonitrile was added, the solid was broken up with a spatula and the solution was stirred for 30 minutes. The solution was filtered and the solid was washed with acetonitrile and ether. Upon drying, 130 mg of 3-(1,6-dihydro-6-oxo-9H-purin-9-yl)-1-[1,4-dioxa-8-azaspiro[4.5]-dec-8-yl]propanone (AIT-0052) as a pure white solid was obtained. Yield: 37%.

EXAMPLE 19
Synthesis of
3-(1,6-dihydro-6-oxo-9H-purin-9-yl)propanoic acid hydrazide (AIT-0056)

1.181 g (5.00 mmol) of 3-(1,6-dihydro-6-oxo-9H-purin-9-yl)propionic acid, ethyl ester (AIT-0027) was placed into a 25 ml flask equipped with a magnetic stirring bar. About 5 ml absolute ethanol was added and then 2.50 g (50.00 mmol) of hydrazine hydrate was added and the solution was stirred at room temperature in a closed flask. A large amount of precipitate formed after about 30 minutes and the solution was allowed to stand overnight. The solution was filtered by vacuum and the white solid was washed with ethanol and then with ether. Upon drying, 0.890 g of 3-(1,6-dihydro-6-oxo-9H-purin-9-yl)propanoic acid hydrazide (AIT-0056) as a white solid was obtained. Yield: 80%.

EXAMPLE 20
Synthesis of
3-(1,6-dihydro-6-oxo-9H-purin-9-yl)-N-(2-aminoethyl)-propanamide (AIT-0058)

1.500 g (25.0 mmol) of ethylenediamine was stirred at room temperature with 250 mg (1.06 mmol) of 3-(1,6-dihydro-6-oxo-9H-purin-9-yl)propionic acid, ethyl ester (AIT-0027) for one hour. The solution was treated with 4 ml acetonitrile and 20 ml of ether with stirring. Upon filtration and washing with ether, this yielded 245 mg of 3-(1,6-dihydro-6-oxo-9H-purin-9-yl)-N-(2-aminoethyl)-propanamide (AIT-0058) as a slightly yellow solid. Yield: 92%.
m.p.: 215°–219° C. (dec.)

EXAMPLE 21
Synthesis of
3-(1,6-dihydro-6-oxo-9H-purin-9-yl)-N-(2-hydroxypropyl) propanamide (AIT-0059)

0.500 g (6.66 mmol) DL-1-amino-2-propanol and 0.250 (1.06 mmol) 3-(1,6-dihydro-6-oxo-9H-purin-9-yl)propionic acid, ethyl ester (AIT-0027) were heated together in a 10 ml round bottom flask with stirring at 120° C. for one hour. The solution was allowed to cool to room temperature and 10 ml acetonitrile was added and the solution was stirred. The solution was triturated with a small amount of methanol (approximately 1 ml) and was stirred until the appearance of a fine white precipitate. The solution was filtered and the white solid was washed with acetonitrile and then with ether. Upon drying, 240 mg of 3-(1,6-dihydro-6-oxo-9H-purin-9-yl)-N-(2-hydroxypropyl)propanamide (AIT-0059) as a white solid was obtained. Yield: 85%. m.p. −212°–216° C.

EXAMPLE 22
Synthesis of
3-(1,6-dihydro-6-oxo-9H-purin-9yl)-N-(2-hydroxypropyl)propanamide (AIT-0060)

0.500 g (5.15 mmol) of furfurylamine and 0.250 g (1.06 mmol) of 3-(1,6-dihydro-6-oxo-9H-purin-9-yl)propionic acid, ethyl ester (AIT-0027) were heated at 120° C. for two hours with stirring. The solution was allowed to cool to room temperature and 10 ml acetonitrile was added and the solution was stirred. The precipitate was collected by filtration and the white solid was washed with acetonitrile and then with ether. Upon drying, 170 mg of 3-(1,6-dihydro-6-oxo-9H-purin-9-yl)-N-(2-hydroxypropyl)propanamide (AIT-0060) as a white solid was obtained.

EXAMPLE 23
Synthesis of
3-(1,6-dihydro-6-oxo-9H-purin-9-yl)-N-(2,3-dihydroxyprop-1-yl)propanamide (AIT-0062)

0.500 g (5.49 mmol) of 3-amino-1,2-propanediol was placed into a 10 ml round bottom flask with a magnetic stirring bar. The flask was heated to 110° C. and 0.250 g (1.06 mmol) of 3-(1,6-dihydro-6-oxo-9H-purin-9-yl)propionic acid, ethyl ester (AIT-0027) was added to the stirring solution. The solution was stirred at 100°–110° C. for one hour. The flask was allowed to cool to room temperature and 10 ml of 1:1 acetonitrile/methanol was added and the solution was stirred vigorously for 30 minutes. The resulting white precipitate was collected using Buchner funnel filtration to yield 272 mg of 3-(1,6-dihydro-6-oxo-9H-purin-9-yl)-N-(2,3-dihydroxyprop-1-yl)propanamide (AIT-0062) as a white solid. 91% yield. m.p. 232°–235° C. (dec.).

EXAMPLE 24
Synthesis of
3-(1,6-dihydro-6-oxo-9H-purin-9-yl)-N-[(2-pyridinyl)-methyl]propanamide (AIT-0063)

0.500 g (4.62 mmol) of 2-(aminomethyl)pyridine and 0.250 g (1.06 mmol) of 3-(1,6-dihydro-6-oxo-9H-purin- 9-yl)propionic acid, ethyl ester (AIT-0027) were heated together with stirring in a 10 ml round bottom flask at 110° C. for 90 minutes. The solution solidified and was cooled to room temperature. 10 ml of acetonitrile was added and the solid was broken up with a spatula until a fine white precipitate was formed. The solid was collected by Buchner vacuum filtration and the solid was washed with acetonitrile and ether to yield 267 mg of 3-(1,6-dihydro-6-oxo-9H-purin-9-yl)-N-[(2-pyridinyl)-methyl]propanamide (AIT-0063) as a white solid. Yield: 84%.

EXAMPLE 25

Synthesis of 3-(1,6-dihydro-6-oxo-9H-purin-9-yl)-N-[2-(diethylamino)ethyl]propanamide (AIT-0064)

0.500 g (4.30 mmol) of N,N-diethylethylenediamine was placed into a 10 ml round bottom flask equipped with a magnetic stirring bar. The amine was heated to 110° C. and 0.250 g (1.06 mmol) of 3-(1,6-dihydro-6-oxo-9H-purin-9-yl)propionic acid, ethyl ester (AIT-0027) was added to the stirring solution. The solution was heated for one hour at 110° C. and was allowed to cool to room temperature. 10 ml of acetonitrile was added and the solution was stirred for 15 minutes. The white precipitate was obtained by filtration and was washed with acetonitrile and then with ether. Upon drying, 195 mg of 3-(1,6-dihydro-6-oxo-9H-purin-9-yl)-N-[2-(diethylamino)ethyl]propanamide (AIT-0064) as a white solid was obtained. Yield: 60%.

EXAMPLE 26

Synthesis of 3-(1,6-dihydro-6-oxo-9H-purin-9-yl)-N-[2-[[2-(2-oxopyrrolidin-1-yl)-1-oxoethyl]amino]ethyl]propanamide (AIT-0065)

3.00 g (19.09 mmol) of methyl-2-oxo-1-pyrrolidine acetate and 11.47 g (190.9 mmol) of ethylenediamine were stirred in a 50 ml round bottom flask at room temperature for 20 hours. The excess ethylenediamine was removed by reduced pressure at 50° C. This yielded 0.620 g (3.35 mmol) of a highly viscous slightly yellow oil, N-(2-aminoethyl)-3-(2-oxo-1-pyrrolidinyl)acetamide. This oil was added to a 10 ml round bottom flask with a magnetic stirring bar, and heated to 140° C. Then 0.250 g (1.06 mmol) of 3-(1,6-dihydro-6-oxo-9H-purin-9-yl)propanoic acid, ethyl ester (AIT-0027) was added. The solution quickly became homogeneous and the temperature was reduced to about 120° C. The reaction was continued for 135 minutes. 8 ml of anhydrous ether were added to the solution, triturated with methanol until a white precipitate formed. The solution was vacuum filtered, and the white solid was washed with acetonitrile and ether. The product, 300 mg (0.8 mmol) of 3-(1,6-dihydro-6-oxo-9H-purin-9-yl)-N-[2-[[2-2-oxopyrrolidin-1-yl)-1-oxoethyl]amino]ethyl]propanamide (AIT-0065) was pure white, and extremely soluble in water. Yield: 75%.

EXAMPLE 27

Synthesis of 3-(1,6-dihydro-6-oxo-9H-purin-9-yl)-N-piperonyl-propanamide (AIT-0066)

0.500 g (3.31 mmol) of piperonylamine was placed into a 10 ml round bottom flask with a magnetic stirring bar and heated to 110° C. and 0.250 g (1.06 mmol) of 3-(1,6-dihydro-6-oxo-9H-purin-9-yl)propionic acid, ethyl ester (AIT-0027) was added to the stirring amine. The solution was heated for 40 minutes at which time the reaction mixture had solidified. 10 ml of acetonitrile was added to the residue and the solution was stirred for about 20 min. The white precipitate was collected by Buchner vacuum filtration and was washed with acetonitrile and then with ether. This yielded 245 mg of (AIT-0066) as a white solid. Yield: 68%.

EXAMPLE 28

Synthesis of 3-(1,6-dihydro-6-oxo-9H-purin-9-yl)-N-[2-(1-pyrrolidinyl)ethyl]propanamide (AIT-0068)

0.500 g. (4.38 mmol) of 1-(2-aminoethyl)-pyrrolidine was heated 100°–110° C. with 0.250 g (1.06 mmol) of 3-(1,6-dihydro-6-oxo-9H-purin-9-yl)propionic acid, ethyl ester (AIT-0027) in a 10 ml round bottom flask with stirring for one hour. Then, 10 ml of acetonitrile was added and the solution was stirred for 15 minutes. The resulting precipitate was collected by vacuum filtration. The solid was washed with acetonitrile and then with ether to yield 275 mg of 3-(1,6-dihydro-6-oxo-9H-purin-9-yl)-N-[2-(1-pyrrolidinyl)ethyl]propanamide (AIT-0068) as a white solid. Yield: 85%.

EXAMPLE 29

Synthesis of N,N',N''-tri[2-[3-(1,6-dihydro-6-oxo-9H-purin-9-yl)-1-oxopropyl]aminoethyl]amine 0.750 g (3.17 mmol) of 3-(1,6-dihydro-6-oxo-9H-purin-9-yl)propionic acid, ethyl ester (AIT-0027) was placed into a 25 ml round bottom flask equipped with a magnetic stirring bar. Then 3 ml of methanol was added along with 28 mg (0.57 mmol) of NaCN and 157 mg (1.07 mmol) of tris (2-aminoethyl)amine. The solution was heated to reflux with stirring under $N_2$. The solution rapidly became homogeneous (approximately 15 minutes) at reflux. After 48 hours, an additional 3–4 ml methanol was added to the residue. The bulk of the residue remained insoluble at reflux and the solution was refluxed for an additional 20 hours. The solution was allowed to cool to room temperature and 20 ml of acetonitrile was added. A white solid precipitated from the solution and was collected by filtration. The solid was washed with acetonitrile and ether to yield 57 mg of an off-white solid. An additional 20 ml acetonitrile was added to the oily residue along with 3 ml methanol. The solution was stirred and heated to reflux until a copious precipitate (off-white) had formed and was free from any oil chunks. Upon filtering, washing with acetonitrile and ether, 686 mg of an orange solid was obtained. The solid sample was dissolved in a minimum amount of water and was chromatographed on 16 g of silica-gel eluting with 90% methanol/10% $H_2O$. All fractions containing the product were combined and evaporated. Acetonitrile was added to the solid residue and the solution was filtered. The solid was washed with either to yield 170 mg of N,N',N''-tri[2-[3-(1,6-dihydro-6-oxo-9H-purin-9-yl)-1-oxopropyl]aminoethyl]amine (AIT-0069) as a free-flowing non-hygroscopic white solid. Yield: 22%

19

EXAMPLE 30

Synthesis of 3-(1,6-dihydro-6-oxo-9H-purin-9-yl)-N-[[2-(1-piperidinyl)]ethyl]-propanamide (AIT-0070)

0.500 g (3.90 mmol) of 1-(2-aminoethyl)piperidine was added to a 10 ml round bottom flask equipped with a magnetic stirring bar. The amine was heated to 100°–110° C. and 0.250 g (1.06 mmol) of 3-(1,6-dihydro-6-oxo-9H-purin-9-yl)propionic acid, ethyl ester (AIT-0027) was added to the stirring solution. The solution was heated for one hour at which time it had solidified. The solution was allowed to cool to room temperature and 10 ml of acetonitrile was added to the solid. This mixture was stirred and the solid was collected by Buchner vacuum filtration. The white crystalline solid was washed with acetonitrile and then with ether to yield 290 mg of 3-(1,6-dihydro-6-oxo-9H-purin-9-yl)-N-[[2-(1-piperidinyl)]ethyl]propanaide (AIT-0070). Yield: 86%.

EXAMPLE 31

Synthesis of 3-(1,6-dihydro-6-oxo-9H-purin-9-yl)-N-[2-(2,2'-diethanolamino)ethyl]-propanamide (AIT-0071)

0.500 g (3.37 mmol) of N,N-bis(2-hydroxyethyl)ethylenediamine was added to a 10 ml round bottom flask equipped with a magnetic stirring bar. The amine was heated to 110° C. and 0.250 g (1.06 mmol) of 3-(1,6-dihydro-6-oxo-9H-purin-9-yl)propionic acid, ethyl ester (AIT-0027) was added to the stirring solution. The solution was heated for one hour and was cooled to room temperature. 20 ml ether was added to the residue and methanol was added dropwise to the stirring solution until a copious white precipitate had formed. The solution was allowed to stir until there were no more chunks. The solution was filtered and the pure white solid was washed with acetonitrile and ether to yield 200 mg of 3-(1,6-dihydro-6-oxo-9H-purin-9-yl)-N-[2-(2,2'-diethanolamino)ethyl]propanamide (AIT-0071). Yield: 56%.

EXAMPLE 32

Synthesis of 3-(1,6-dihydro-6-oxo-9H-purin-9-yl)-N-[2-(1H-indol-3-yl)ethyl]propanamide (AIT-0072)

0.700 g (4.37 mmol) of tryptamine were placed into a 50 ml round bottom flask equipped with a magnetic stirring bar. Then 5.0 ml of dimethylsulfoxide were added to dissolve the tryptamine. After all the tryptamine had gone into solution, 1.0 g (3.04 mmol) of 3-(1,6-dihydro-6-oxo-9H-purin-9-yl)propanoic acid, 4-nitrophenyl ester (AIT-0081) was added and the flask was sealed with a ground glass stopper. The mixture was stirred at room temperature for five hours. The reaction mixture was poured into 60 ml of acetone. The product was filtered, washed twice with 10 ml of acetone and air dried. The yield of 3-(1,6-dihydro-6-oxo-9H-purin-9-yl)-N-[2-(1H-indol-3-yl)ethyl]-propanamide (AIT-0072) was 0.813 g. Yield: 48% (Purity 99.3%). mp: 204°–206° C.

EXAMPLE 33

Synthesis of 2-[(1,6-dihydro-6-amino-9H-purin-9-yl)methyl]-butanedioic acid, methyl diester. (AIT-0073)

5.00 g (37.00 mmol) of adenine was placed into a 110 ml round bottom flask equipped with a magnetic stirring bar and reflux condenser. Then 70 ml anhydrous methanol was added along with 40 mg of sodium metal. The solution was stirred until all of the sodium was consumed. Then 23.41 g (0.148 mmol) of dimethyl itaconate was added and the solution was heated to reflux. Reflux was continued for two days. The solution was transferred to a 250 ml flask and 50 ml of methanol and an additional 80 mg of sodium metal was added. The solution was heated to reflux. After several hours, the reaction was stopped and cooled to room temperature. The solid was collected by Buchner vacuum filtration and washed with methanol and then with ether. Upon drying, 8.10 g of 2-[(1,6-dihydro-6-amino-9H-purin-9-yl)methyl]butanedioic acid, methyl diester (AIT-0073) as a white free flowing crystalline solid was obtained. Yield: 75% m.p. 185°–187° C.

EXAMPLE 34

Synthesis of 3-(1,6-dihydro-6-oxo-9H-purin-9-yl)-N-(3-aminopropyl)propanamide (AIT-0074).

0.250 g (1.06 mmol) of 3-(1,6-dihydro-6-oxo-9H-purin-9-yl)propionic acid, ethyl ester (AIT-0027) was added to 1.85 g (25.0 mmol) of 1,3-diaminopropane in a 10 ml round bottom flask equipped with a magnetic stirring bar. The solution was stirred at room temperature for two hours. 10 ml ether was added and the solution was stirred for a few minutes. The ether solution was decanted, leaving an oil residue. 5 ml of acetonitrile and 4 ml of ether were added and the solution was stirred. Methanol was added dropwise until a precipitate had formed. The solution was filtered and washed with acetonitrile and ether, to yield 205 mg of 3-(1,6-dihydro-6-oxo-9H-purin-9-yl)-N-(3-aminopropyl)-propanamide (AIT-0074). m.p. 172°–175° C. Yield: 73%

EXAMPLE 35

Synthesis of 3-[(1,6-dihydro-6-oxo-9H-purin-9-yl)methyl]butanedioic acid, methyl diester (AIT-0075)

2.00 g (6.82 mmol) of 2-[(1,6-dihydro-6-amino-9H-purin-9-yl)methyl]butanedioic acid, dimethyl ester (AIT-0073) was placed into a 50 ml round bottom flask equipped with a magnetic stirring bar. Then 10 ml glacial acetic acid was added and the solution was stirred until homogeneous. 2.35 g (34.10 mmol) of NaNO₂ in 4 ml of H₂O was added to the stirring solution dropwise. The stoppered solution was stirred for 24 hours at room temperature. An additional 0.775 g (11.23 mmol) of NaNO₂ in 1 ml H₂O was added and the solution was stirred for another 24 hours. The acetic acid was removed under reduced pressure on the rotary evaporator. Water was added and was removed in the same manner. This was repeated again until little or no more acetic acid was left. 10 ml of H₂O was added to the semi-solid residue to completely dissolve the mixture. This solution was extracted with 30 ml-40 ml of acetonitrile and the aqueous layer was discarded. The organic layer was washed twice with 30 ml of saturated brine.

Upon evaporation of the solvent, a light orange oil was obtained. This was treated with 35 ml of ethyl ether and triturated with methanol to yield 615 mg of 3-[(1,6-dihydro-6-oxo-9H-purin-9-yl)methyl]butanedioicacid, methyl diester (AIT-0075) as an off-white solid. Yield: 31% m.p. 130°–135° C.

EXAMPLE 36

Synthesis of 4-[[3-(1,6-dihydro-6-oxo-9H-purin-9-yl)-1-oxopropyl]amino]benzoic acid, ethyl ester (AIT-0079)

165 mg (0.50 mmol) of 3-(1,6-dihydro-6-oxo-9H-purin-9-yl)propanoic acid, 4-nitrophenyl ester (AIT-0081) and 84 mg (0.50 mmol) of 4-aminobenzoic acid ethyl ester were heated together in 1.5 ml of dimethylsulfoxide at 35°–40° C. for 72 hours. A white precipitate was observed at the bottom of the flask. 10 ml acetone was added and the solid was collected by Buchner vacuum filtration. The solid was washed twice with acetone and was allowed to dry. This yielded 53 mg of 4-[[3-(1,6-dihydro-6-oxo-9H-purin-9-yl)-1-oxopropyl]amino]benzoic acid, ethyl ester (AIT-0079) as a white solid. m.p. 265°–269° C. Yield: 30%.

EXAMPLE 37

Synthesis of 3-(1,6-dihydro-6-oxo-9H-purin-9-yl)propanoic acid (AIT-0080)

20.00 g (84.66 mmol) of 3-(1,6-dihydro-6-oxo-9H-purin-9-yl)propanoic acid, ethyl ester (AIT-0027) was placed into a 500 ml round bottom flask equipped with a magnetic stirring bar. 150 ml of water was added to the flask and the solution stirred. To the stirring heterogeneous solution was added 10.46 g (0.1854 mol) of KOH pellets. Within a few minutes the solution became a homogeneous light green color. The solution was stirred at room temperature for 3.5 hours. The solution was acidified (pH approximately 1.0) with concentrated HCl. The precipitated solution was placed at 4° C. overnight. The solid was collected by filtration, washed sequentially with water, methanol and ether, and dried. 17.63 g (84.7 mmol) of 3-(1,6-dihydro-6-oxo-9H-purin-9-yl)propanoic acid (AIT-0080) was obtained as a free flowing white solid. Yield: 100%.

EXAMPLE 38

Synthesis of 3-(1,6-dihydro-6-oxo-9H-purin-9-yl)propanoic acid, 4-nitrophenyl ester (AIT-0081)

7.00 g (0.03363 mol) of 3-(1,6-dihydro-6-oxo-9H-purin-9-yl)propanoic acid (AIT-0080) was added to a 250 ml round bottom flask equipped with a magnetic stirring bar. 70 ml of anhydrous pyridine was added and the solution was stirred. To the resulting heterogeneous solution was added 11.46 g (0.04876 mol) of 4-nitrophenyl trifluoromethyl acetate under a stream of nitrogen. The solution was stirred at 30° C. for 17 hours. The resulting thick slurry was cooled to room temperature and 175 ml of distilled H$_2$O was added to the stirring solution. The solution became homogeneous and then a precipitate formed. The mixture was placed in the freezer for several hours (<0° C.). The solution was removed from the freezer and was allowed to thaw. The solid was collected by filtration and was washed with H$_2$O, methanol and ether. Upon drying, 10.32 g of 3-(1,6-dihydro-6-oxo-9H-purin-9-yl)propanoic acid, 4-nitrophenyl ester (AIT-0081) as a white solid was obtained. Yield: 93%.

EXAMPLE 39

Synthesis of 4-[[3-(1,6-dihydro-6-oxo-9H-purin-9-yl)-1-oxopropyl]amino]benzoic acid (AIT-0082)

8.88 g (24.99 mmol) of 4-[[3-(1,6-dihydro-6-oxo-9H-purin-9-yl)-1-oxopropyl]amino]benzoic acid, ethyl ester (AIT-0079) was placed into a 500 ml round bottom flask with 180 ml water and a magnetic stirring bar. To the stirring solution, 135 ml of a 0.53 molar KOH(aq.) solution was added dropwise over a period of one hour. The solution was stirred at room temperature for 3.5 hours. The solution was brought to approximately pH 3.0 with dilute HCl and was then vacuum filtered. The resulting fine white solid was washed with water and subsequently methanol. Upon drying under vacuum at approximately 45° C., 7.34 g (22.4 mmol) of a white solid, 4-[[3-(1,6-dihydro-6-oxo-9H-purin-9-yl)-1-oxopropyl]amino]benzoic acid (AIT-0082) was obtained. mp: 319°–321° C. Yield: 90%.

EXAMPLE 40

Synthesis of 4-[[3-(1,6-dihydro-6-oxo-9H-purin-9-yl)-1-oxopropyl]amino]benzoic acid compd. with 1-(dimethylamino)-2-propanol (1:1) (AIT-0083)

7.34 g (22.42 mmol) of 4-[[3-(1,6-dihydro-6-oxo-9H-purin-9-yl)-1-oxopropyl]amino]benzoic acid (AIT-0082) was placed in a 500 ml round bottom flask equipped with a magnetic stirring bar. 25 ml of water was added and the white slurry was stirred. 18.6 g, 180.3 mmol of 1-(dimethylamino)-2-propanol (AIT-1000) was added to the stirring slurry. The solution rapidly became homogeneous and the reaction was continued for 90 minutes at room temperature. Acetone (350 ml) was then added, and the stirring solution triturated with methanol until a copious white precipitate formed. The product was collected by vacuum filtration and washed with acetone. After drying, 9.45 g (22.0 mmol) of 4-[[3-(1,6-dihydro-6-oxo-9H-purin-9-yl)-1-oxopropyl]amino]benzoic acid compd. with 1-(dimethylamino)-2-propanol (1:1) (AIT-0083) was obtained. Yield: 98%.

EXAMPLE 41

Synthesis of 4-[[3-(1,6-dihydro-6-oxo-9H-purin-9-yl)-1-oxopropyl]amino]benzoic acid, 1-(dimethylamino)-2-propyl ester (AIT-0084)

2.0 g (5.78 mmol) of 4-[[3-(1,6-dihydro-6-oxo-9H-purin-9-yl)-1-oxopropyl]amino]benzoic acid (AIT-0082) were placed into a 100 ml round bottom flask equipped with a magnetic stirring bar, reflux condenser and a drying tube. 16 ml of thionyl/chloride were added and the mixture was slowly heated to 55°–60° C. for six hours. The reaction mixture was allowed to cool to room temperature. 50 ml of benzene were added to break up the crystal mass. The solid was collected by filtration, washed twice with 10 ml of benzene and was allowed to dry under the hood for two hours. While the product was being dried, 20 ml of dimethylamino-2-propanol were placed in a 100 ml round bottom flask equipped with a magnetic stirring bar and drying tube. The mass was slowly added under stirring conditions.

The drying tube was replaced on the flask and the stirring continued for six hours at room temperature. The reaction mixture was poured into a 500 ml Erlenmeyer flask containing 300 ml of acetonitrile. The solution was stirred for five minutes. The flask was covered with parafilm and was allowed to stand in the hood overnight at room temperature. The solid material was removed by filtration, washed twice with 15 ml of acetonitrile and air dried under the hood for three hours. The weight of the product 4-[[3-(1,6-dihydro-6-oxo-9H-purin-9-yl)-1-oxopropyl]amino]benzoic acid, 1-(dimethylamino)-2-propyl ester (AIT-0084) was 830 mg. Yield: 33%

EXAMPLE 42

Synthesis of
2-[[3-(1,6-dihydro-6-oxo-9H-purin-9-yl)-1-oxopropyl]amino]-3-phenylpropanoic acid, methyl ester (AIT-0085).

0.500 g (1.519 mmol) of 3-(1,6-dihydro-6-oxo-9H-purin-9-yl)propanoic acid, 4-nitrophenyl ester (AIT-0081) and 0.328 g (1.519 mmol) of L-phenylalanine methyl ester hydrochloride were placed in a 25 ml round bottom flask equipped with a magnetic stirring bar. 3 ml of dimethylsulfoxide was added and the solution was stirred to dissolve as much solid as possible at room temperature. Then 159 mg (1.571 mmol) of triethylamine was added and the solution was stirred at room temperature (20° C.) for one hour. 10 ml of acetonitrile was added to the stirring solution. The solution was triturated with ether until a white precipitate had formed. The solution was filtered to remove the triethylamine hydrochloride. The mother liquor was again treated with ether to produce a precipitate. The mixture was filtered and the white solid was washed with ethyl ether and dried. This yielded 0.465 g of a white solid. The white solid material was added to 22 ml ethanol/H$_2$O 9:1 and was heated to dissolve the compound. After allowing to cool to room temperature, ether was added until just before the cloud point. The solution was placed in a refrigerator overnight. Upon filtration and washing with ether, 0.235 g of 2-[[3-(1,6-dihydro-6-oxo-9H-purin-9-yl)-1-oxopropyl]amino]-3-phenylpropanoic acid, methyl ester (AIT-0085) as a white crystalline material was obtained. m.p. 186°–191° C.

EXAMPLE 43

Synthesis of
2-[[3-(1,6-dihydro-6-oxo-9H-purin-9-yl)-1-oxopropyl]amino]-3-phenylpropanoic acid (AIT-0086)

100 mg (0.271 mmol) of 2-[[3-(1,6-dihydro-6-oxo-9H-purin-9-yl)-1-oxopropyl]amino]-3-phenylpropanoic acid, methyl ester (AIT-0085) were placed into a 10 ml beaker equipped with a magnetic stirring bar. Water (5 ml) was added to the beaker and stirring was started. To the stirring heterogeneous mixture was added 100 mg (1.79 mmol) of KOH pellets. Within a few seconds the reaction mixture became a homogeneous green color. Stirring was continued for one hour. The pH of the solution was adjusted to 2.0 with concentrated hydrochloric acid. The product was collected by vacuum filtration and washed twice with 2 ml of water and then twice with 2 ml of acetone. The weight of the product, 2-[[3-(1,6-dihydro-6-oxo-9H-purin-9-yl)1-oxopropyl]amino]-3-phenylpropanoic acid (AIT-0086), was 80 mg. Yield: 83%. m.p. 240°–242° C.

EXAMPLE 44

Synthesis of
3-(1,6-dihydro-6-oxo-9H-purin-9-yl)-N-[2-(2-deoxy-glucopyranosyl)]propanamide (AIT-0087)

0.300 (0.911 mmol) of 3-(1,6-dihydro-6-oxo-9H-purin-9-yl)propanoic acid, 4-nitrophenyl ester (AIT-0081) and 0.196 g (0.911 mmol) of D-glucosamine HCl were placed into a 10 ml round bottom flask with a magnetic stirring bar and 2 ml of dimethylsulfoxide. Then 100 mg (0.988 mmol) of triethylamine was added and the solution was stirred (closed flask) at room temperature for one hour. The solution was stirred for one hour at 20° C. and the product was precipitated from the reaction mixture by adding 10 ml of acetonitrile with stirring. The product was collected by vacuum filtration and the solid washed with acetonitrile and then with ether. Upon drying, 345 mg of 3-(1,6-dihydro-6-oxo-9H-purin-9-yl)-N-[2-(2-deoxy-glucopyranosyl)]propanamide (AIT-0087) as a white free flowing solid was obtained. Yield: 103%.

EXAMPLE 45

Synthesis of
4-[[2-[[3-(1,6-dihydro-6-oxo-9H-purin-9-yl)-1oxo-propyl]amino]ethyl]amino]-2-hydroxy-4-oxo-N,N,N-trimethyl-1-butanaminium chloride (AIT-0090)

248 mg (1.0344 mmol) of 4-[(2-aminoethyl)amino]-2-hydroxy-4-oxo-N,N,N-trimethyl-1-butanaminium chloride was placed into a 10 ml round bottom flask with magnetic stirring bar. Then 2 ml of dimethylsulfoxide was added and the solution was gently heated to help dissolve the amine. 340 mg (1.034 mmol) of 3-(1,6-dihydro-6-oxo-9H-purin-9-yl)propanoic acid, 4-nitrophenyl ester (AIT-0081) was added to the stirring solution. The solution was stirred for a period of one hour and 3 ml of methanol was added. Then 3 ml of acetone was added and the solution was filtered. The solid was washed several times with acetone and allowed to dry. This yielded 105 mg of 4-[[2-[[3-(1,6-dihydro-6-oxo-9H-purin-9-yl)-1-oxopropyl]amino]ethyl]amino]-2-hydroxy-4-oxo-N,N,N-trimethyl-1-butanaminium chloride (AIT-0090) as a white solid. m.p. approximately 260–265 (dec) Yield: 33%.

EXAMPLE 46

Synthesis of
4-[[3-(1,6-dihydro-6-oxo-9H-purin-9-yl)-1-oxopropyl]amino]butanoic acid, methyl ester (AIT-0092)

0.300 g (0.9111 mmol) of 3-(1,6-dihydro-6-oxo-9H-purin-9-yl)propanoic acid, 4-nitrophenyl ester (AIT-0081) and 0.142 g (0.925 mmol) of gamma amino butyric acid, methyl ester hydrochloride were placed into a 10 ml round bottom flask with a magnetic stirring bar and 2 ml dimethylsulfoxide. To this solution was added 0.100 g (0.988 mmol) of triethylamine. The solution immediately turned green and was stirred at room temperature for one hour. Then 5 ml of acetone was added and the solution was filtered. The mother liquor was treated with ether (approximately 35 ml) to precipitate the product. Upon filtration and washing with ether, 232 mg of a white solid 4-[[3-(1,6-dihydro-6-oxo-9H-purin-9-yl)-1-oxopropyl]amino]butanoic acid, methyl ester (AIT-0092) was obtained. Yield: 83%.

EXAMPLE 47

Synthesis of
3-[[3-(1,6-dihydro-6-oxo-9H-purin-9-yl)-1-oxopropyl-]amino]propane sulfonic acid (AIT-0093)

0.300 g (0.9111 mmol) of 3-(1,6-dihydro-6-oxo-9H-purin-9-yl)propanoic acid, 4-nitrophenyl ester (AIT-0081) and 0.127 g (0.9111 mmol) of 3-amino-1-propane sulfonic acid were placed into a 10 ml round bottom flask with 2 ml of dimethylsulfoxide and a magnetic stirring bar. To this solution was added 0.100 g (0.988 mmol) of triethylamine and the solution immediately turned green. The solution was stirred at room temperature for five hours. Dimethylsulfoxide was removed in vacuo with gentle heating. 9 ml of acetone was added and the solution was triturated with methanol until homogeneous. No precipitate had formed. The solution was transferred to a 50 ml round bottom flask with 10 ml acetone and 5 ml methanol. Ether was added until just before the cloud point and the flask was placed into freezer overnight (<0° C.).

EXAMPLE 48

Synthesis of
1-[2-[[3-(1,6-dihydro-6-oxo-9H-purin-9-yl)-1-oxopropyl]hydrazino]2-oxoethyl]pyridinium chloride (AIT-0094)

0.300 g (0.9111 mmol) of 3-(1,6-dihydro-6-oxo-9H-purin-9-yl)propanoic acid, 4-nitrophenyl ester (AIT-0081) and 0.172 g (0.9166 mmol) of Girard's reagent P were placed into a 10 ml round bottom flask with 2 ml dimethylsulfoxide and a magnetic stirring bar. The solution was heated to 70° C. with stirring. As the solution began to warm up, the solids began to dissolve and the solution became progressively green in color. After about 30 minutes, the solution was completely homogeneous. The solution was allowed to react at 70° C. for four hours and was allowed to cool to room temperature. 10 ml acetonitrile was added and a white precipitate formed immediately. The solution was filtered and washed with acetonitrile and ether. The solid was allowed to dry but it absorbed H2O from the atmosphere. The hygroscopic effect could either be due to residual dimethylsulfoxide or the product itself.

EXAMPLE 49

Synthesis of
4-[[3-(1,6-dihydro-6-oxo-9H-purin-9-yl)-1-oxopropyl]amino]-N-[2-(diethylamino)ethyl]benzamide monohydrochloride (AIT-0095)

0.300 g (0.9111 mmol) of 3-(1,6-dihydro-6-oxo-9H-purin-9-yl)propanoic acid, 4-nitrophenyl ester (AIT-0081) was placed into a 10 ml round bottom flask with 0.250 g (0.9198 mmol) of procainamide hydrochloride. 2 ml of dimethylsulfoxide was added and the solution was heated to 40° C. for four days. The solution was then poured into 40 ml acetone and was stirred vigorously for 20 minutes. The solid was collected by vacuum filtration and washed with acetone. The solid was placed into a 25 ml round bottom flask with 5 ml ethanol and was stirred for 15 minutes. The solid was collected by vacuum filtration and washed with ethanol and then with ether. This yielded 133 mg of 4-[[3-(1,6-dihydro-6-oxo-9H-purin-9-yl)-1-oxopropyl]amino]-N-[2-(diethylamino)ethyl]-benzamide monohydrochloride (AIT-0095) as a slightly yellow non-hygroscopic solid. m.p. 210°-213° C. (no decomposition).

EXAMPLE 50

Synthesis of
3-(1,6-dihydro-6-oxo-9H-purin-9-yl)-N-(2-oxothiaolan-3-yl)propanamide (AIT-0096)

0.300 g (0.9111 mmol) of 3-(1,6-dihydro-6-oxo-9H-purin-9-yl)propanoic acid, 4-nitrophenyl ester (AIT-0081) and 142 mg (0.9242 mmol) of DL-homocysteine thiolactone hydrochloride were placed into a 10 ml round bottom flask equipped with a magnetic stirring bar. Then 100 mg (0.9882 mmol) of triethylamine was added and the solution was stirred at room temperature (closed flask) for three hours. 2 ml acetonitrile was added to the solution as it was stirred. The solution was triturated with ether until a small amount of precipitate had formed. The solution was filtered and the mother liquor was precipitated with 30 ml ether. Upon filtration and washing with ether, 306 mg of a white solid was obtained. The 306 mg of material obtained above was placed into a 10 ml round bottom flask with a magnetic stirring bar and 5 ml acetonitrile. The solution was stirred for 20 minutes at room temperature. The solution was filtered and the solid was washed with chloroform to yield 235 mg of 3-(1,6-dihydro-6-oxo-9H-purin-9-yl)-N-(2-oxothiaolan-3-yl)propanamide (AIT-0096) as a white solid. Yield: 84%. m. p. 228°-230° (sharp).

EXAMPLE 51

Synthesis of
3-(1,6-dihydro-6-oxo-9H-purin-9-yl)-N-[2-(3,4-dihydroxyphenyl)-2-hydroxyethyl]propanamide (AIT-0097)

0.300 g (0.9111 mmol) of 3-(1,6-dihydro-6-oxo-9H-purin-9-yl)-propanoic acid, 4-nitrophenyl ester (AIT-0081) and 0.190 g (0.924 mmol) of (R)-(−)-norepinephrine hydrochloride were placed into a 10 ml round bottom flask with 2 ml dimethylsulfoxide and a magnetic stirring bar. 128 mg (1.26 mmol) of triethylamine was added and the solution was stirred at room temperature for one hour. 10 ml of chloroform was added and a copious yellow precipitate formed immediately. The solution was stirred for several minutes and was filtered by vacuum. The resulting solid was washed with chloroform and allowed to dry. After drying, 359 mg of a yellow solid, 3-(1,6-dihydro-6-oxo-9H-purin-9-yl)-N-[2-(3,4-dihydroxyphenyl)-2-hydroxyethyl]propanamide (AIT-0097) was obtained. Yield: 110%.

EXAMPLE 52

Synthesis of
3-(1,6-dihydro-6-oxo-9H-purin-9-yl)-1-(1-phenyl-4-oxo-1,3,8-triazaspiro[4.5]dec-8-yl)-propanone (AIT-0098)

0.300 g (0.9111 mmol) of 3-(1,6-dihydro-6-oxo-9H-purin-9-yl)-propanoic acid, 4-nitrophenyl ester (AIT-0081) and 0.212 g (0.9165 mmol) of 1-phenyl-1,3,8-triazaspiro[4.5]decane-4-one were placed into a 10 ml round bottom flask equipped with a magnetic stirring bar. 2 ml of dimethylsulfoxide (dried over barium oxide) was added and the solution was stirred in a closed flask at room temperature for 20 hours. The reaction was allowed to proceed overnight to ensure completion. The solvent was removed with vacuum using gentle heat (approximately 45 deg.). 10 ml ethyl acetate was added to the stirring residue (oil) and a copious white precipitate formed immediately. The solution was stirred for 30 minutes to ensure homogeneity. Upon filtration, washing with ethyl acetate, and drying, 345 mg of a free flowing white solid, 3-(1,6-dihydro-6-oxo-9H-purin-9-yl)-1-(1-phenyl-4-oxo-1,3,8-triazaspiro[4.5]-dec-8-yl)propanone (AIT-0098) was obtained. Yield: 90%.

EXAMPLE 53

Synthesis of 3-(1,6-dihydro-6-oxo-9H-purin-9-yl)-1-(1,2,3,4-tetrahydro-2-azacarbazo-2-yl)propanone (AIT-0099)

0.300 g (0.9111 mmol) of 3-(1,6-dihydro-6-oxo-9H-purin-9-yl)-propanoic acid, 4-nitrophenyl ester (AIT-0081) and 0.157 g (0.9111 mmol) of 1,2,3,4-tetrahydro-9H-pyrido[3,4-b]indole were placed in a 10 ml round bottom flask equipped with a magnetic stirring bar. 2 ml of dimethylsulfoxide (dried over barium oxide) was added and the solution was stirred at room temperature for three hours. 10 ml of ethyl acetate was added to the solution and the solution placed into the freezer for two days to crystallize. The crystalline mass was broken up with a spatula and vacuum filtered. The crystals were washed with acetone and ether to yield 280 mg of a tan solid. The solid was recrystallized from boiling ethanol and allowed to cool to room temperature and then 0° overnight. 205 mg of a crystalline off-white solid 3-(1,6-dihydro-6-oxo-9H-purin-9-yl)-1-(1,2,3,4-tetrahydro-2-azacarbazo-2-yl)propanone ((AIT-0099) was obtained. Yield: 85%. MP: 185–190 (dec.)

EXAMPLE 54

Synthesis of 3-(1,6-dihydro-6-oxo-9H-purin-9-yl)-N-[2-(3,4-dihydroxyphenyl)-2-hydroxyethyl]-N-methylpropanamide (AIT-0100).

0.300 g (0.9111 mmol) of 3-(1,6-dihydro-6-oxo-9H-purin-9-yl)propanoic acid, 4-nitrophenyl ester (AIT-0081) and 0.167 g (0.9111 mmol) of (R)-(−)-epinephrine were placed into a 10 ml round bottom flask with 2 ml dimethylsulfoxide (dried over barium oxide) and a magnetic stirring bar. The solution was stirred at room temperature (25°) and was initially heterogeneous. After about 45 minutes, as the epinephrine began to react with AIT-0081, the solution was a nearly homogeneous yellow orange color. The solution was stirred an additional two hours, drawn into a pasteur pipet, and added with stirring to a flask containing 50 ml acetone and a magnetic stirring bar. A copious white precipitate formed and the solution was stirred for ten minutes. The solution was filtered by vacuum and the white solid washed with acetone. The Buchner funnel was immediately placed under high vacuum to remove small traces of dimethylsulfoxide. 120 mg of a white solid, 3-(1,6-dihydro-6-oxo-9H-purin-9-yl)-N-[2-(3,4-dihydroxyphenyl)-2-hydroxyethyl]-N-methylpropanamide (AIT-0100), was obtained. Yield: 48%.

EXAMPLE 55

Synthesis of 3-(1,6-dihydro-6-oxo-9H-purin-9-yl)-1-(2-phenylimidazo-1-yl)propanone (AIT-0102)

0.300 g (0.9111 mmol) of 3-(1,6-dihydro-6-oxo-9H-purin-9-yl)propanoic acid, 4-nitrophenyl ester (AIT-0081) and 0.133 g (0.9111 mmol) of 2-phenyl-2-imidazoline were placed into a 10 ml round bottom flask with 2 ml dry dimethylsulfoxide and a magnetic stirring bar. The solution was stirred at room temperature, and the reaction was allowed to proceed for a total time of one hour; then 12 ml acetone was added. The solution was filtered and the solid washed with acetone. Upon drying, 275 mg of a white solid, 3-(1,6-dihydro-6-oxo-9H-purin-9-yl)-1-(2-phenylimidazo-1-yl)propanone (AIT-0102), was obtained. Yield: 90%. m.p.: 192°–197°.

EXAMPLE 56

Synthesis of 1-[3-(1,6-dihydro-6-oxo-9H-purin-9-yl)-1-oxopropyl]-3-piperidinecarboxylic acid, ethyl ester (AIT-0103)

0.300 g (0.9111 mmol) of 3-(1,6-dihydro-6-oxo-9H-purin-9-yl)propanoic acid, 4-nitrophenyl ester (AIT-0081) was placed into a 10 ml round bottom flask with 2 ml dry dimethylsulfoxide and a magnetic stirring bar. 150 mg of (+ −)-ethylnipecotate was added to the solution. The solution immediately turned green and was stirred at room temperature (25°) for two hours. The dimethylsulfoxide was removed under reduced pressure with gentle heating. 10 ml of ether was added to the yellow residue and the solid was broken up with a spatula. The solution was stirred until a fine white homogeneous precipitate was obtained. The solution was filtered and the solid washed with ether to yield 285 mg of 1-[3-(1,6-dihydro-6-oxo-9H-purin-9-yl)-1-oxopropyl]-3-piperidinecarboxylic acid, ethyl ester (AIT-0103) as a white solid. Yield: 90%. m.p.: 171°–175°.

EXAMPLE 57

Synthesis of 4-[[3-(1,6-dihydro-6-oxo-9H-purin-9-yl)-1-oxopropyl]amino]benzoic acid, 1-(dimethylamino)-2-propyl ester, monohydrochloride (AIT-0105)

0.300 g (0.9111 mmol of 3-(1,6-dihydro-6-oxo-9H-purin-9-yl)propanoic acid, 4-nitrophenyl ester (AIT-0081) and 0.245 g (0.9468 mmol) of 4-aminobenzoic acid, 1-(dimethylamino)-2-propyl ester (AIT-0104) were placed into a 5 ml flask with 2 ml dry dimethylsulfoxide, a small magnetic stirring bar, and a thermometer. The solution was heated to 75° for 23 hours. The dimethylsulfoxide was removed under vacuum with heating. 3 ml of acetonitrile and 2 ml of methanol were added to the remaining dark viscous residue. After stirring at room temperature for several minutes, a tan precipitate was formed and the solution was filtered and the solid washed with acetonitrile. Upon drying, 85 mg of 4-[[3-(1,6-dihydro-6-oxo-9H-purin-9-yl)-1-oxopropyl]amino]benzoic acid, 1-(dimethylamino)-2-propyl ester, monohydrochloride (AIT-0105) as a tan solid was obtained. m.p.: 270°–275°.

EXAMPLE 58

Synthesis of 3-(1,6-dihydro-6-oxo-9H-purin-9-yl)propanoic acid, 1-(dimethylamino)-2-propyl ester (AIT-0106)

0.300 g (1.441 mmol) of 3-(1,6-dihydro-6-oxo-9H-purin-9-yl)propanoic acid (AIT-0080) and 0.305 g (1.478 mmol) of dicyclohexylcarbodiimide were placed into a 10 ml round bottom flask equipped with magnetic stirring bar and thermometer. 4 ml of N,N-dimethylacetamide and 0.168 g (1.628 mmol) of 1-dimethyamino-2-propanol were added and the solution was heated to 75° (closed flask) for two hours. The solution was allowed to come to room temperature and a large amount of precipitate formed. The contents were transferred to a larger flask with 20 ml of acetone. 20 ml of ether was added and the solution was allowed to cool down in the refrigerator. Crystals formed within a short period of time. A solid was obtained by filtration and washed with ether. 408 mg of 3-(1,6-dihydro-6-oxo-9H-purin-9-yl)propanoic acid, 1-(dimethylamino)-2-propyl ester (AIT-0106) as a white crystalline solid was obtained. Yield: 97%. m.p.: 280°–284°.

EXAMPLE 59

Synthesis of
2-[[3-(1,6-dihydro-6-oxo-9H-purin-9-yl)-1-oxopropyl-]amino]-3-(5-hydroxyl-1H-indol-3-yl)-propionic acid
(AIT-0111)

100 mg (0.500 mmol) of DL-5-hydroxytryptophan and 3 ml of dry dimethylsulfoxide were placed in a 25 ml round bottom flask equipped with a magnetic stirring bar and stopper. Then 150 mg (0.456 mmol) of 3-(1,6-dihydro-6-oxo-9H-purin-9-yl)propanoic acid, 4-nitrophenyl ester (AIT-0081) were added and the heterogeneous mixture was stirred for 2.5 hours at room temperature in the closed flask. The mixture became completely homogeneous. The reaction mixture was poured into 20 ml of acetone and a semi-solid precipitate was obtained by filtration. The crude product was washed twice with 2 ml of acetone. The solid was resuspended in 10 ml of acetone and the insoluble material was removed by filtration. The acetone solution was evaporated to dryness. The yield of product 2-[[3-(1,6-dihydro-6-oxo-9H-purin-9-yl)-1-oxopropyl]amino]-3-(5-hydroxyl-1H-indol-3-yl)-propionic acid (AIT-0111) was 15 mg. Yield: 7.3% (Purity 93%).

As illustrated by the foregoing examples and in Appendix A, and as will be appreciated by those skilled in the art, the structures of the exemplary compounds of the present invention are composed of two chemical structural moieties linked by what is believed to be a biodegradeable bridge. Each of the two distinct chemical moieties consists of the active chemical structural core of a specific type of biologically active molecule. It was originally believed that these compounds would generally function as pro-drug delivery compounds. In contrast to the prior art pro-drug delivery systems utilizing biologically active compounds embedded in physical biodegradeable matrices, the compounds of the present invention were intended to function as their own delivery system. Additionally, it was also believed that these compounds would be able to cross the blood-brain barrier by virtue of containing the hypoxanthine chemical core. Moreover, because each of the biologically active chemical moieties of the compounds were designed to be biologically active in their own right as well as to serve as a carrier vehicle, it was believed that the compounds would be able to treat neurological conditions as well as immunological conditions. As noted above, it was also anticipated that the biodegradeable linkage chemically bridging the two biologically active moieties would be hydrolyzed, enabling the individual moieties to function independently.

However, as will be detailed in the following examples, completely unexpected biological activities were observed for these compounds and it is now hypothesized that the respective active cores of each compound may remain linked. Though considerable research will be necessary to prove or disprove this hypothesis, it is now believed that the respective active cores of each linked compound simultaneously interacts with adjacent or structurally close receptor sites on treated cells and neurons. The uniquely dose-dependent activity, biological properties, and diverse specific biological effects of these compounds are indicative of such unusual and unexpected interactive mechanisms.

More specifically, when the biological activities of the exemplary compounds of the present invention were compared to those of their closest chemical analogs, completely unexpected results were obtained. These results are detailed in the following non-limiting exemplary biological assays and data tables of neuroimmunologic acitivity including immune response, memory function and locomotor stimulation. For ease of presentation, the closest analogous compounds have been identified as AIT-001 and AIT-1000 and are, respectively, hypoxanthine and 4-(acetylamino)benzoic acid, compd with 1-(dimethylalmino)-2-propanol (1:1) or DIP-P-a-c-B-a (as disclosed in U.S. Pat. No. 4,221,910).

ASSAY FOR MEMORY FUNCTION

The effects of AIT compounds on memory were evaluated utilizing the winshift test paradigm which utilizes foraging behavioral strategy which is inherent in mice (Ordy, J. M., et al., Neurobiol. of Aging, 9: 667–683, 1988). The test is based upon the fact that after the hungry animal goes to a particular place and eats all the food there, it will go to a different place on the next trial to continue the search for food. By alternating the reward site and modifying the inter-trial interval, one can determine if the subject animal can remember which of the two arms of a T-maze it had just been in during the previous trial. Mice are food deprived to 80% of free feeding body weight. They are placed in the start box and thirty seconds later the door is opened and the animal is free to travel to the choice point. Then it will enter one of the two goal boxes. In this study both of the goal boxes contain 0.5 cc of milk during the first training trial. After entering the goal box, a door will close to prevent the subject from leaving. The animal is allowed to drink all of the milk. Then it is removed from the maze and after a delay of 90 seconds, the subject is again placed in the start box. Ten trials are run under each condition. A score of 50% is considered chance; that is, the subject does not remember which box it was in on the previous trial. The latency time to leave the start box is recorded as a measure of motivation, the running time (the time from leaving the start box to reaching the goal box) is recorded as a measure of performance, and the number of correct responses as an index of memory. Past experience indicates that few mice with saline treatment (control group) will score above chance on the 90 second inter-trial delay. Drug treatment is given intraperitoneally 60 minutes prior to trial. The results of this assay were tabulated in the following table.

TABLE 1

Summary of Memory Performance Testing

| Delay (sec) | Treatment | Dose (mg/kg) | Motivation Latency (sec)[1] | Performance Run Time (sec)[1] | % Correct Treated | % Correct Group Control | Drug Effect[2] |
|---|---|---|---|---|---|---|---|
| 90 | Composite Control[3] | | 3.19 | 2.46 | | | |
| | AIT-083 | 1 | 5.75 | 4.96 | 58 | 61 | |
| | | 0.5 | 11.63* | 3.76 | 60 | 35 | + |
| | | 0.1 | 2.25 | 2.15 | 48 | 43 | |
| | AIT-082 | 0.5 | 1.95 | 2.20 | 65 | 38 | + |
| | | 0.1 | 1.71 | 1.65 | 40 | 33 | |
| | AIT-034 | 0.5 | 15.14* | 11.22* | 67 | 57 | |
| | AIT-065 | 0.5 | 8.96 | 7.36* | 60 | 49 | |
| | AIT-080 | 0.5 | 12.81* | 14.99* | 65 | 40 | + |
| | AIT-110 | 0.5 | 21.68* | 6.35 | 72 | 45 | + |
| | AIT-001 | 0.5 | 2.38 | 4.05 | 45 | 50 | |
| | AIT-1000 | 0.5 | 10.44* | 10.08* | 75 | 50 | + |

[1]Motivation: * = latency time of treated group 3× > control
Performance: * = time to run maze of treated group 3× > control
[2]Memory: % correct: + = score of treated group > control by 50%
[3]Composite control represents mean of 11 series of controls

ASSAY FOR LOCOMOTOR ACTIVITY

To evaluate the effect of the various compounds on spontaneous locomotor activity, mice were injected i.p. with one of the compounds (0.5 mg/kg) or an equal volume (0.1 ml/10 gm body weight) of saline (Ritzmann, R. F., Walter, R., Bhargava, H. M. and Flexner, L. B., Blockage of narcotic-induced dopamine receptor supersensitivity by cyclo (Leu-Gly), Proc. Natl. Acad. Sci. USA 76: 5997-8, 1979). Activity was recorded for one hour using a Varimex activity apparatus, Columbus Instruments, Columbus, Ohio, and tabulated into the following table.

TABLE 2

| Compound | Locomotor Activity Counts/hr ± S.E.M. | P value[(1)] |
|---|---|---|
| Control | 323 ± 59 | |
| AIT-001 | 402 ± 120 | NS |
| AIT-034 | 428 ± 86 | NS |
| AIT-065 | 644 ± 114 | 0.03 |
| AIT-080 | 525 ± 109 | 0.06 |
| AIT-082 | 415 ± 85 | NS |
| AIT-083 | 698 ± 133 | 0.03 |
| AIT-110 | 301 ± 57 | NS |
| AIT-1000 | 430 ± 139 | NS |

[(1)]NS = not significant statistically from control

BIOLOGICAL ACTIVITY

LYMPHOCYTE PROLIFERATION ASSAY FOR IMMUNE FUNCTION

Lymphocytes are one of the most important cells that protect the body from infectious diseases and cancer. The determination of the functionality of the lymphocytes has been widely used as a measurement of the healthy status of the body. The ability of drugs to enhance or impair the function of lymphocytes has been predictive of their therapeutic efficacy. (Tsang, P. H., Tangnavarad, K., Solomon, S., and Bekesi, J. G.: Modulation of T- and B-Lymphocyte Functions by Isoprinosine in Homosexual Subjects with Prodromata and in Patients with Acquired Immune Deficiency Syndrome (AIDS). J. Clin. Immunol. 4:469-478, 1984.)

Peripheral blood (50 ml) was obtained from volunteers by venipuncture utilizing a plastic syringe containing 15 units/ml preservative-free heparin. Peripheral blood lymphocytes were separated by Ficoll-Hypaque gradient centrifugation. (Tsang, P. H., Holland J. F., and Bekesi, J. G.: Central role of T lymphocytes in specific recognition of tumor antigens in $^{51}$Cr-leukocyte adherence inhibition. Cell. Immunol. 73:365-375, 1982.) Essentially, 50 ml of blood was diluted with an equal volume of saline, overlaid onto a 25 ml Ficoll-Hypaque gradient and centrifuged at 850 g and 20° C. for 45 minutes. The lymphocytes in the buffy-coat interface were collected, washed twice in saline and resuspended in RPMI-1640 media supplemented with 20% heat-inactivated autologous or heat-inactivated pooled AB plasma.

Lymphocyte functions were determined by blastogenic responses induced by two mitogens: highly purified phytohemagglutinin (PHA; Wellcome, Dartford, England) for T-lymphocyte functions and pokeweed mitogen (PWM; Wellcome, Dartford, England) for T cell-dependent B-lymphocyte function. (Ref.: Hadden, J. W., Lopez, C., O'Reilly, R. J. and Hadden, E. M.: Levamisole and inosiplex: Antiviral agents with immunopotentiating action. Ann. NY Acad. Sci. 284:139-152, 1977.) Mononuclear cells ($1 \times 10^5$ cells/0.1 ml of RPMI-1640) were cultured in triplicate in microplates in the presence of optimal stimulatory concentrations of PHA (0.5 microgram) or PWM (0.75 microgram) at 37° C. in a humidified atmosphere containing 5% $CO_2$ in air. Control cultures were incubated without mitogens. Lymphocyte blastogenesis was determined by measuring the level of DNA synthesis after the addition of 1 microcurie of [$H^3$]thymidine(TdR) to each well 18 hours prior to the termination of culture (64 hours for PHA- and 96 hours for PWM-induced reactions). Following incubation, the cells were harvested with a Marsh II automatic harvester on glass-fiber filters and the amount of [$H^3$]TdR incorporated was determined in a Packard liquid scintillation spectrometer. Results are expressed as counts per minute (cpm) per $10^5$ lymphocytes. The various test compounds were incorporated into the incubation media at the beginning of the culture at the concentrations indicated.

The results were then tabulated in Tables 3 and 4 as cpm for control cultures and as % stimulation or inhibition when compared to the corresponding controls. The results are also expressed as either enhancing (+), suppressing (−), or having no effect on the proliferation of T-lymphocyte and/or B-lymphocyte function.

TABLE 3

Effect on Mitogen-induced Lymphoproliferative Response

| Compound | Dose (ug/ml) | Control Value[1] | % Stimulation | Activity[2] |
|---|---|---|---|---|
| T-cell Response (PHA) | | | | |
| Control | | 110,000 | | |
| AIT-001 | 100 | | 39% | + |
| AIT-034 | 100 | | 8 | 0 |
| AIT-083 | 7 | | 57 | + |
| B-cell Response (PWM) | | | | |
| Control | | 69,368 | | |
| AIT-001 | 100 | | 29% | + |
| AIT-034 | 100 | | 0 | 0 |
| AIT-083 | 7 | | 0 | 0 |

[1]Counts per minute (cpm) per $10^5$ lymphocytes
[2]+ = stimulation of 12% or greater as compared to untreated control

TABLE 4

Effect on Mitogen-induced Lymphoproliferative Response

| Compound | Control Value[1] 0 | Dose (ug/ml.) % Change from Control | | | | | Activity[2] |
|---|---|---|---|---|---|---|---|
| | | 1 | 2.5 | 5 | 10 | 25 | 100 | |
| T-cell response (PHA) | | | | | | | | |
| AIT-080 | 127,374 | 7 | 4 | 3 | 16 | 4 | 11 | + |
| AIT-110 | 110,110 | 0 | 0 | −8 | 11 | 9 | 10 | 0 |
| AIT-082 | 148,687 | 7 | 7 | 2 | 12 | 12 | 11 | + |
| AIT-065 | 129,487 | 11 | 8 | 8 | 19 | 2 | −5 | + |
| AIT-1000 | 131,487 | 2 | 2 | 9 | 6 | 7 | 11 | 0 |
| B-cell response (PWM) | | | | | | | | |
| AIT-080 | 109,134 | 24 | 3 | 2 | 11 | 8 | 0 | + |
| AIT-110 | 91,960 | 18 | 4 | −3 | −3 | 5 | 4 | + |
| AIT-082 | 116,251 | 4 | 2 | 5 | 9 | 1 | −4 | 0 |
| AIT-065 | 80,251 | 13 | 16 | 22 | 19 | 14 | 7 | + |
| AIT-1000 | 102,252 | 3 | 5 | 0 | 6 | 8 | −3 | 0 |

[1]Counts per minute (cpm) per $10^5$ lymphocytes
[2]+ = stimulation of 12% or greater as compared to untreated control To further illustrate the uniquely dose-dependent activities of the compounds of the present invention as contrasted to the closest prior art compounds, the foregoing data can be summarized on the basis of immunological response and neurological response as follows:

TABLE 5

SUMMARY OF BIOLOGICAL ACTIVITY

| Cpd. | Immune Response[1] | | | Neurological Response | | | |
|---|---|---|---|---|---|---|---|
| | T-Cell Stim. | B-Cell Stim. | Action Site | Cognitive Function[2] | | | Locomotor Activity[3] |
| | | | | % Corr. | Motiv. | Perform. | |
| AIT-001 | 100 | 100 | tb | 0 | 0 | 0 | 0 |
| AIT-080 | 10 | 1 | TB | + | − | − | + |
| AIT-110 | 0 | 1 | B | + | −− | 0 | 0 |
| AIT-082 | 10 | 0 | T | + | 0 | 0 | 0 |
| AIT-083 | <7 | 0 | T | + | − | 0 | + |
| AIT-1000 | 0 | 0 | 0 | + | − | − | 0 |
| AIT-034 | 0 | 0 | 0 | 0 | − | − | 0 |
| AIT-065 | 10 | 1 | TB | 0 | 0 | − | + |

[1]Dose in micrograms/ml. at which peak stimulation effect is observed in vitro.;
Action site: t = weak T-cell stimulant; T = potent T-cell stimulant; b = weak B-cell stimulant; B = potent B-cell stimulant
[2]% correct: + = score of treated group > control by 50%
Motivation: − = latency time of treated group 3× > control; −− = latency time of treated group 5× > control
Performance: −− = time to run maze of treated group 3× > control
[3]Locomotor activity: + = activity of treated group significantly higher than control group.

From the foregoing, it will be appreciated by those skilled in the art that the exemplary compounds of the present invention discussed above possess uniquely dose-dependent combinations of neuroimmunological properties. For example, as shown in Table 5, compound AIT-080 enhances T-lymphocyte proliferation at a moderate dosage (10 μg/ml), yet enhances B-lymphocyte function at relatively low dosage (1 μg/ml).

Additionally, AIT-080 enhanced memory function as well as locomotor activity at a relatively low dosage (0.5 mg/kg in vivo).

Equally unique functional properties are exhibited by compound AIT-083. At relatively low dosage (7 μg/ml), this compound only stimulated T-lymphocyte proliferation—there was no effect on B-lymphocyte proliferation. At a moderate dosage (1 mg/kg in vivo), AIT-083 had no activity on memory function, yet enhanced memory function at the lower dose at 0.5 mg/kg.

Interestingly, it would be expected that the closest analogs to the active core components of AIT-083 would exhibit similar properties. However, as clearly demonstrated in Table 5, hypoxanthine (AIT-001) and DIP-Pac-BA (AIT-1000) individually exhibited markedly different activities in both quantity and character than the exemplary compounds of the present invention (AIT-082 and AIT-083). On a broader scale, it would also be expected that the exemplary compounds of the present invention would exhibit common properties among themselves, especially if they were to function as pro-drugs which biodegrade into similar active core components. For example, AIT-110 might be degraded to form AIT-080 and/or AIT-001 whereas AIT-083 might be degraded to form AIT-082 and/or AIT-080 and/or AIT-001. However, in direct contrast to these expectations, the foregoing biological activity data as summarized in Table 5 clearly demonstrates that the exemplary compounds exhibit unexpected diverse properties and ranges of activity.

Thus, in accordance with the teachings of the present invention, it is possible to promote B-lymphocyte and/or T-lymphocyte function with or without an associated cognitive enhancement function by administering the appropriate dosage of a single compound of the present invention (in direct contrast to the expected properties of the closest prior art analog compounds). These unique combinations of dose dependent properties make the compounds of the present invention particularly applicable to the treatment of neuroimmunologic disorders such as AIDS, Alzheimer's disease, immune disorders, infectious diseases and the effects of aging.

Although the particular dose, formulation and route of administration to accomplish these results is unique to each mammalian patient and the desires of the attending physician, the foregoing guidelines for the compounds of the present invention describe their usefulness as neuroimmunologic compounds. Generally, when used to treat neuroimmunologic conditions, suitable pharmaceutical compositions containing the appropriate doses of the compositions of the present invention will be administered initially and then modified to determine the optimum dosage for treatment of the particular mammalian patient.

These compounds may be administered to a mammalian patient for treatment of neuroimmunologic conditions either alone or in combination as a pharmaceutical formulation utilizing pharmaceutically acceptable carrier materials such as inert solid diluents, aqueous solutions or non-toxic, organic solvents. If desired, these pharmaceutical formulations may also contain preserving and stabilizing agents and the like.

Having thus described exemplary embodiments of the compounds of the present invention, it should now be apparent to those skilled in the art that the various objects and advantages of the present invention have been attained and that modifications, adaptations and equivalent compositions may be made in view thereof which will fall within the scope and spirit of the present invention. For example, other isomers, analogues and homologues of the compounds of the present invention may be substituted for those disclosed and described herein. Accordingly, the scope of the present invention is defined and limited only by the following claims.

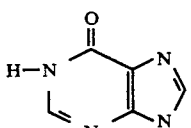

AIT-001 hypoxanthine or purin-6(1H)-one

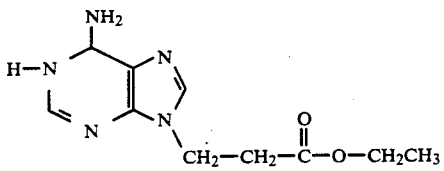

AIT-0026 3-(6-amino-9H-purin-9-yl)propionic acid, ethyl ester

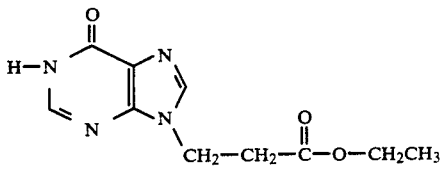

AIT-0027 3-(1,6-dihydro-6-oxo-9H-purin-9-yl)propionic acid, ethyl ester

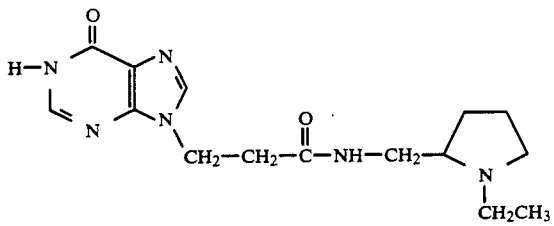

AIT-0029 3-(1,6-dihydro-6-oxo-9H-purin-9-yl)-N-[(1-ethylpyrrolidin-2-yl)methyl]propanamide

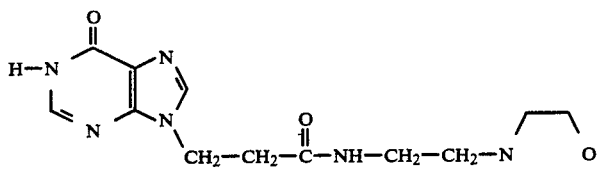

AIT-0031 3-(1,6-dihydro-6-oxo-9H-purin-9-yl)-N-[2-(4-morpholinyl)ethyl]propanamide

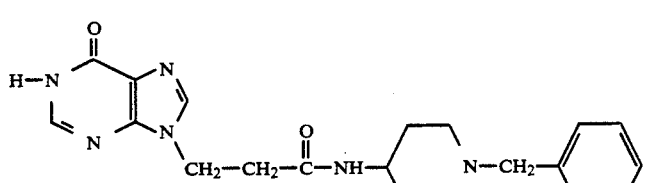

AIT-0033 3-(1,6-dihydro-6-oxo-9H-purin-9-yl)-N-(1-benzylpiperidin-4-yl)propanamide -continued

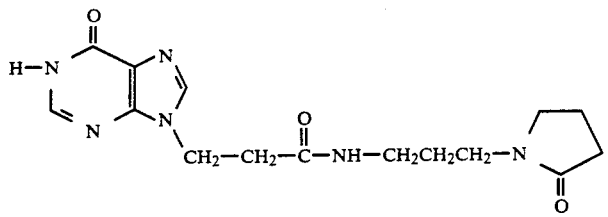
AIT-0034 3-(1,6-dihydro-6-oxo-9H-purin-9-yl)-N-[3-(2-oxopyrrolidin-1-yl)propyl]propanamide

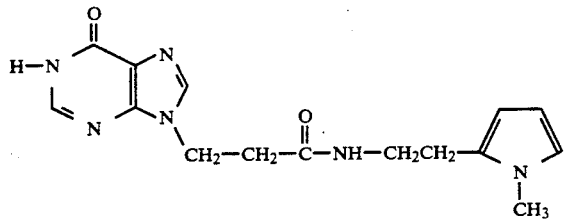
AIT-0035 3-(1,6-dihydro-6-oxo-9H-purin-9-yl)-N-[2-(1-methylpyrrol-2-yl)ethyl]propanamide

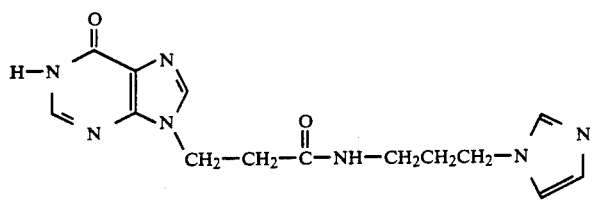
AIT-0037 3-(1,6-dihydro-6-oxo-9H-purin-9-yl)-N-[3-(1-imidazolyl)propyl]propanamide

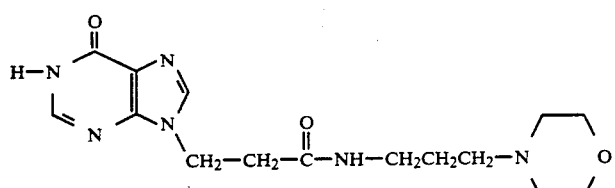
AIT-0043 3-(1,6-dihydro-6-oxo-9H-purin-9-yl)-N-[3-(4-morpholinyl)propyl]propanamide

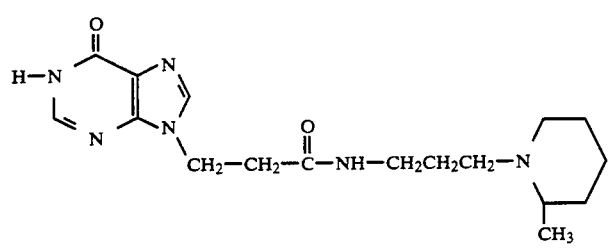
AIT-0044 3-(1,6-dihydro-6-oxo-9H-purin-9-yl)-N-[3-(2-methypiperidin-1-yl)propyl]propanamide

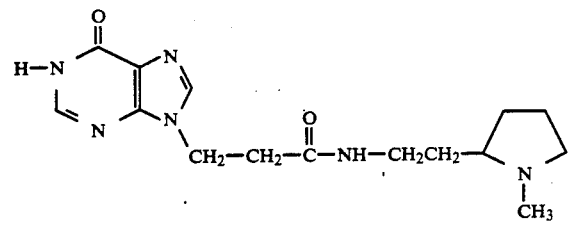
AIT-0045 3-(1,6-dihydro-6-oxo-9H-purin-9-yl)-N-[2-(1-methylpyrrolidin-2-yl)ethyl]propanamide

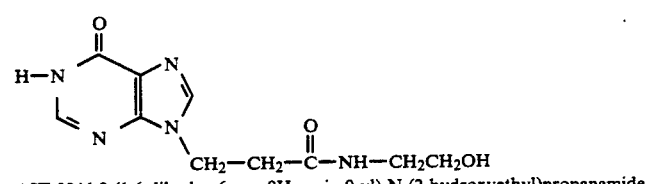
AIT-0046 3-(1,6-dihydro-6-oxo-9H-purin-9-yl)-N-(2-hydroxyethyl)propanamide -continued

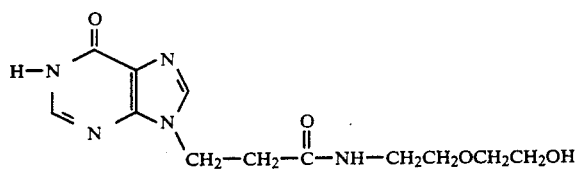
AIT-0047 3-(1,6-dihydro-6-oxo-9H-purin-9-yl)-N-[2-(2-hydroxyethoxy)ethyl]propanamide

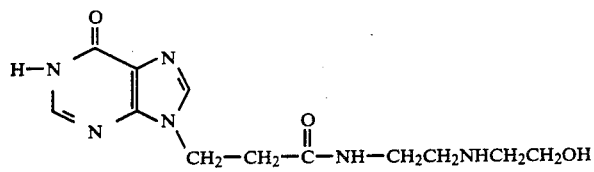
AIT-0048 3-(1,6-dihydro-6-oxo-9H-purin-9-yl)-N-[2-[(2-hydroxyethyl)amino]ethyl]propanamide

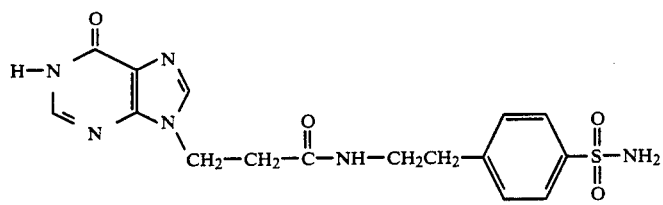
AIT-0049 3-(1,6-dihydro-6-oxo-9H-purin-9-yl)-N-[2-(4-aminosulfonylphenyl)ethyl]propanamide

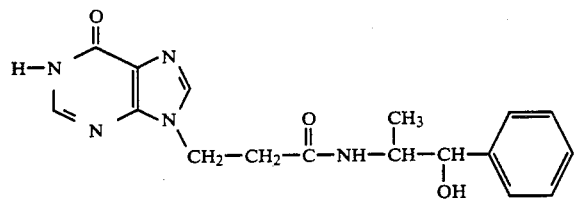
AIT-0050 3-(1,6-dihydro-6-oxo-9H-purin-9-yl)-N-[(2-hydroxy-1-methyl-2-phenyl)ethyl]propanamide

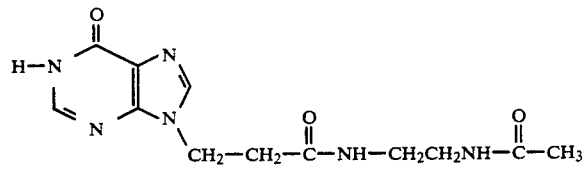
AIT-0051 3-(1,6-dihydro-6-oxo-9H-purin-9-yl)-N-[2-[(1-oxoethyl)amino]ethyl]propanamide

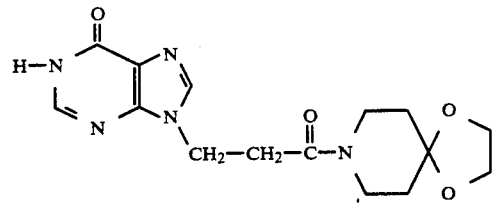
AIT-0052 3-(1,6-dihydro-6-oxo-9H-purin-9-yl)-1-[1,4-dioxa-8-azaspiro[4.5]dec-8-yl]propanone

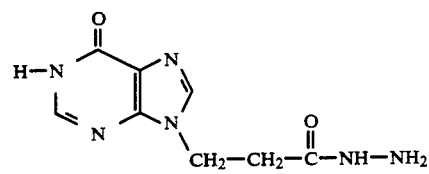
AIT-0056 3-(1,6-dihydro-6-oxo-9H-purin-9-yl)propanoic acid hydrazide

-continued

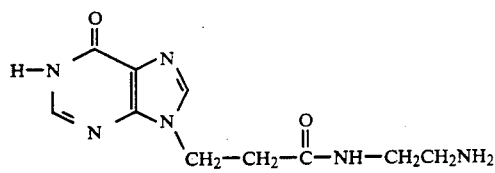
AIT-0058 3-(1,6-dihydro-6-oxo-9H-purin-9-yl)-N-(2-aminoethyl)propanamide

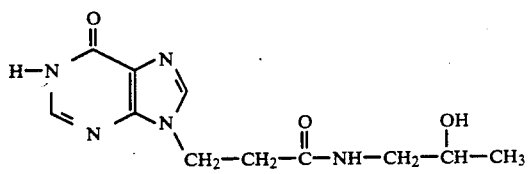
AIT-0059 3-(1,6-dihydro-6-oxo-9H-purin-9-yl)-N-(2-hydroxypropyl)propanamide

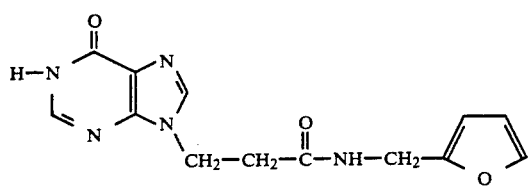
AIT-0060 3-(1,6-dihydro-6-oxo-9H-purin-9-yl)-N-[(2-furanyl)methyl)]propanamide

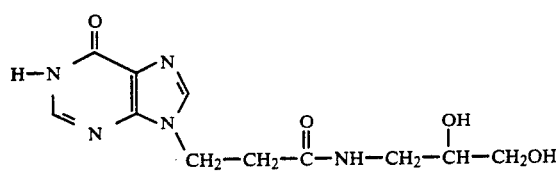
AIT-0062 3-(1,6-dihydro-6-oxo-9H-purin-9-yl)-N-(2,3-dihydroxyprop-1-yl)propanamide

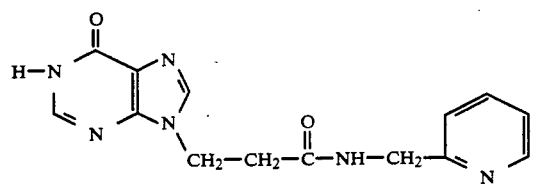
AIT-0063 3-(1,6-dihydro-6-oxo-9H-purin-9-yl)-N-[(2-pyridinyl)methyl]propanamide

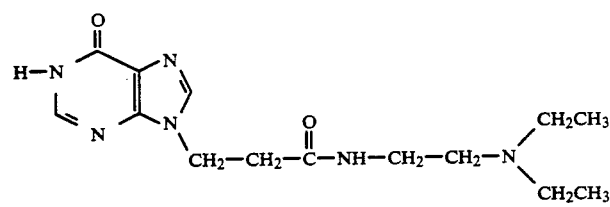
AIT-0064 3-(1,6-dihydro-6-oxo-9H-purin-9-yl)-N-[2-(diethylamino)ethyl]propanamide

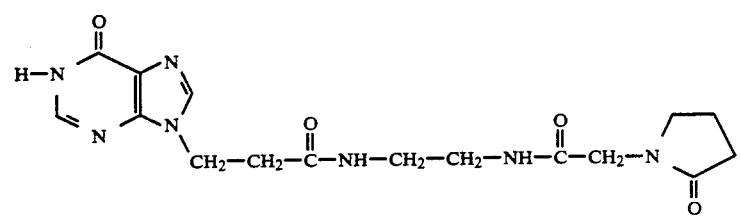
AIT-0065 3-(1,6-dihydro-6-oxo-9H-purin-9-yl)-N-[2-[[2-(2-oxopyrrolidin-1-yl)-1-oxoethyl]amino]ethyl]propanamide

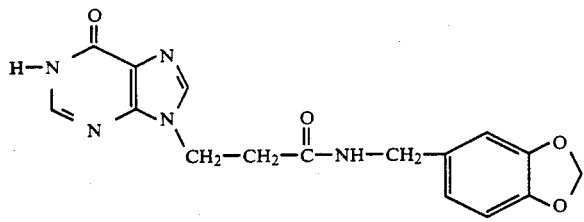
AIT-0066 3-(1,6-dihydro-6-oxo-9H-purin-9-yl)-N-piperonylpropanamide
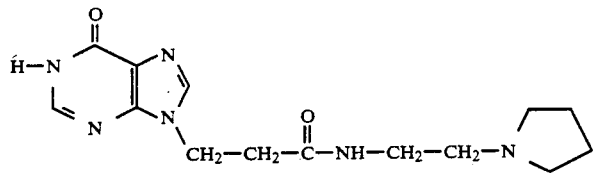
AIT-0068 3-(1,6-dihydro-6-oxo-9H-purin-9-yl)-N-[(1-pyrrolidinyl)ethyl]propanamide
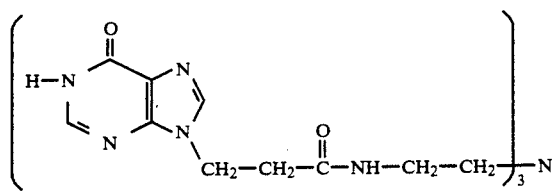
AIT-0069 N,N',N''-tri[2-[3-(1,6-dihydro-6-oxo-9H-purin-9-yl)-1-oxopropyl]aminoethyl]amine
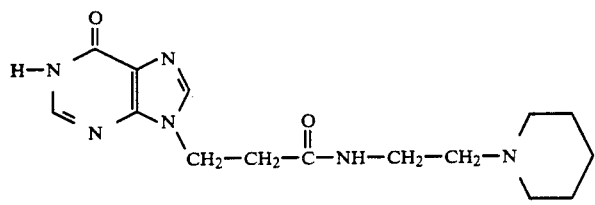
AIT-0070 3-(1,6-dihydro-6-oxo-9H-purin-9-yl)-N-[[2-(1-piperidinyl)]ethyl]propanamide
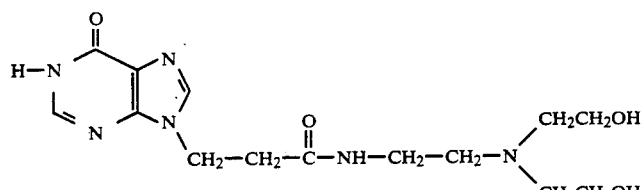
AIT-0071 3-(1,6-dihydro-6-oxo-9H-purin-9-yl)-N-[2-(2,2'-diethanolamino)ethyl]propanamide
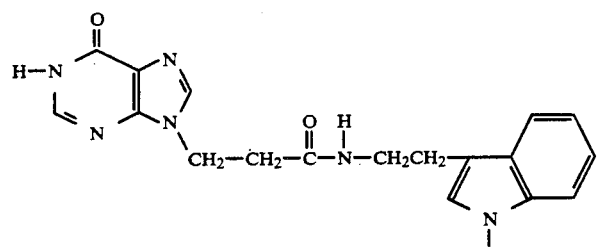
AIT-0072 3-(1,6-dihydro-6-oxo-9H-purin-9-yl)-N-[2-(1H-indol-3-yl)ethyl]propanamide
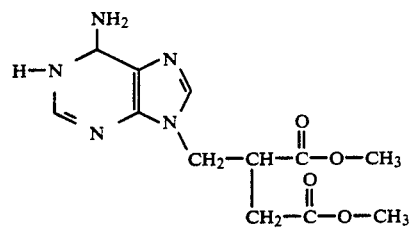

-continued

AIT-0073 2-[(6-amino-9H-purin-9-yl)methyl]butanedioic acid, methyl diester

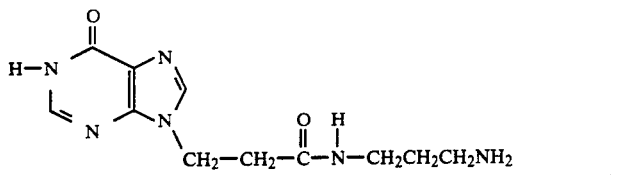

AIT-0074 3-(1,6-dihydro-6-oxo-9H-purin-9-yl)-N-(3-aminopropyl)propanamide

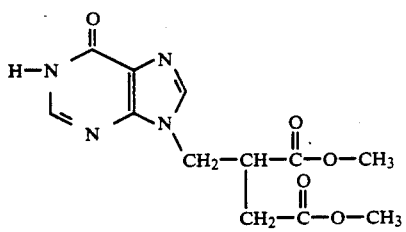

AIT-0075 2-[(1,6-dihydro-6-oxo-9H-purin-9-yl)methyl]butanedioic acid, methyl diester

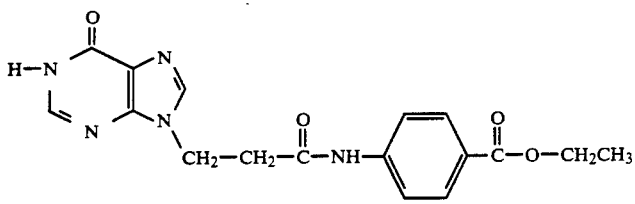

AIT-0079 4-[[3-(1,6-dihydro-6-oxo-9H-purin-9-yl)-1-oxopropyl]amino]benzoic acid, ethyl ester

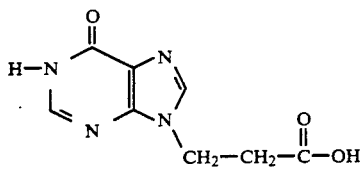

AIT-0080 3-(1,6-dihydro-6-oxo-9H-purin-9-yl)propanoic acid

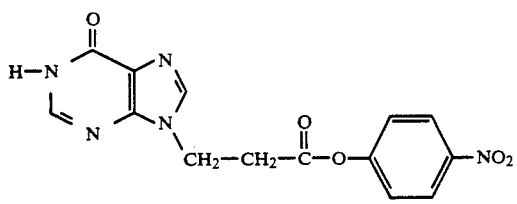

AIT-0081 3-(1,6-dihydro-6-oxo-9H-purin-9-yl)propanoic acid, 4-nitrophenyl ester

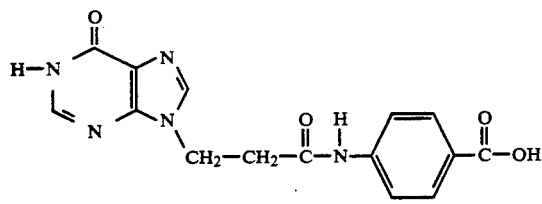

AIT-0082 4-[[3-(1,6-dihydro-6-oxo-9H-purin-9-yl)-1-oxopropyl]amino]benzoic acid

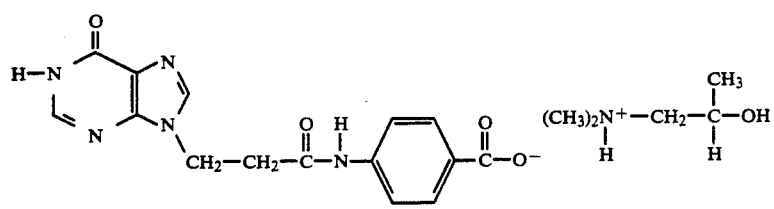

AIT-0083 4-[[3-(1,6-dihydro-6-oxo-9H-purin-9-yl)-1-oxopropyl]amino]benzoic acid compd. with 1-(dimethylamino)-2-propanol(1:1)

-continued

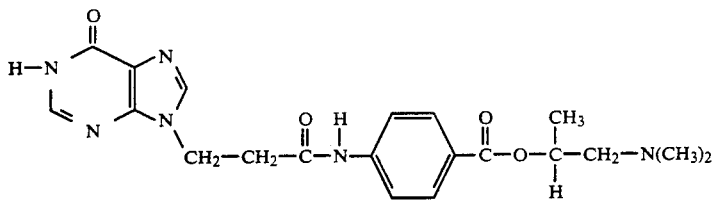

AIT-0084 4-[[3-(1,6-dihydro-6-oxo-9H-purin-9-yl)-1-oxopropyl]amino]benzoic acid, 1-(dimethylamino)-2-propyl ester

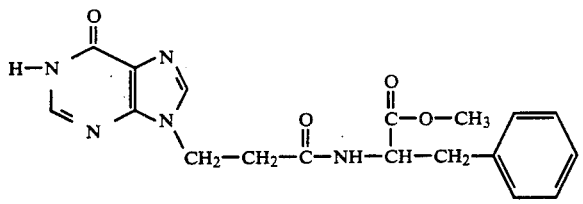

AIT-0085 2-[[3-(1,6-dihydro-6-oxo-9H-purin-9-yl)-1-oxopropyl]amino]-3-phenylpropanoic acid, methyl ester

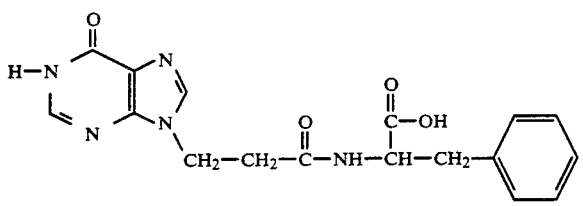

AIT-0086 2-[[3-(1,6-dihydro-6-oxo-9H-purin-9-yl)-1-oxopropyl]amino]-3-phenylpropanoic acid

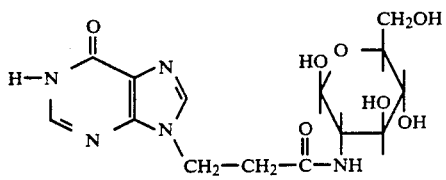

AIT-0087 3-(1,6-dihydro-6-oxo-9H-purin-9-yl)-N-[2-(2-deoxy-glucopyranosyl)]propanamide

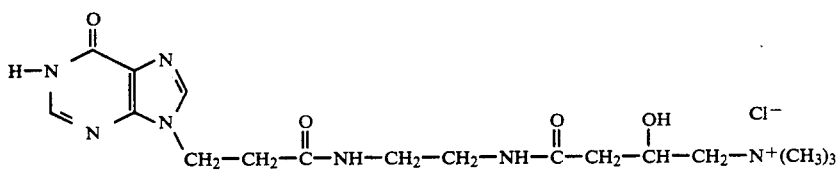

AIT-0090 4-[[2-[[3-(1,6-dihydro-6-oxo-9H-purin-9-yl)-1-oxopropyl]amino]ethyl]amino]-2-hydroxy-4-oxo-N,N,N-trimethyl-1-butanaminium chloride

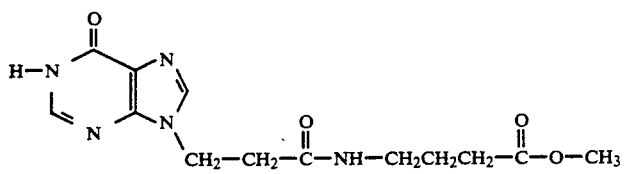

AIT-0092 4-[[3-(1,6-dihydro-6-oxo-9H-purin-9-yl)-1-oxopropyl]amino]butanoic acid, methyl ester

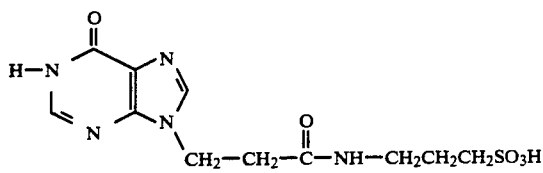

AIT-0093 3-[[3-(1,6-dihydro-6-oxo-9H-purin-9-yl)-1-oxopropyl]amino]propanesulfonic acid -continued

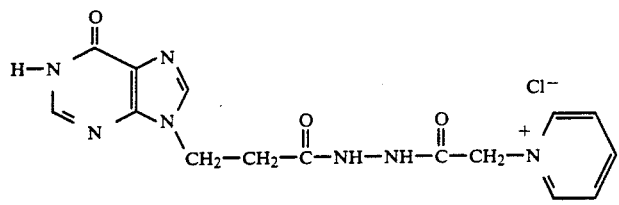

AIT-0094 1-[2-[[3-(1,6-dihydro-6-oxo-9H-purin-9-yl)-1-oxopropyl]hydrazino]2-oxoethyl]pyridinium chloride

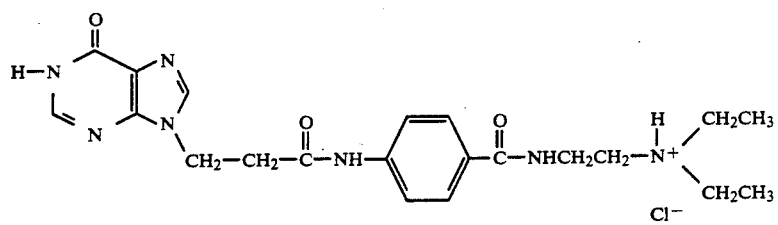

AIT-0095 4-[[3-(1,6-dihydro-6-oxo-9H-purin-9-yl)-1-oxopropyl]amino]-N-[2-(diethylamino)-ethyl]benzamide monohydrochloride

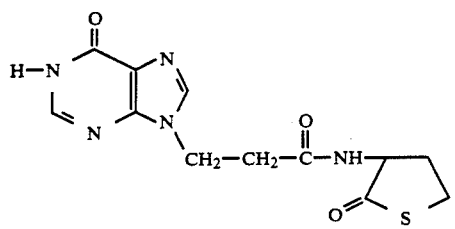

AIT-0096 3-(1,6-dihydro-6-oxo-9H-purin-9-yl)-N-(2-oxothiaolan-3-yl)propanamide

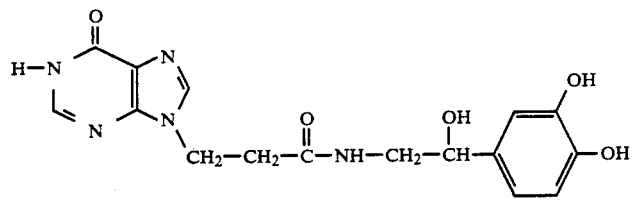

AIT-0097 3-(1,6-dihydro-6-oxo-9H-purin-9-yl)-N-[2-(3,4-dihydroxyphenyl)-2-hydroxyethyl]propanamide

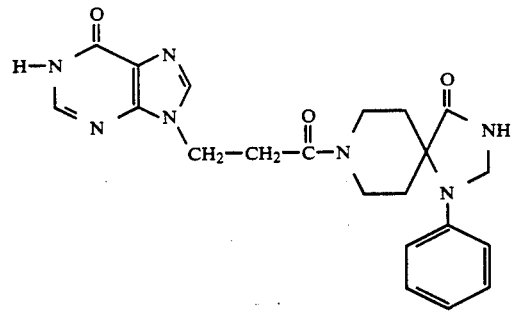

AIT-0098 3-(1,6-dihydro-6-oxo-9H-purin-9-yl)-1-(1-phenyl-4-oxo-1,3,8-triazaspiro[4.5]dec-8-yl)-propanone

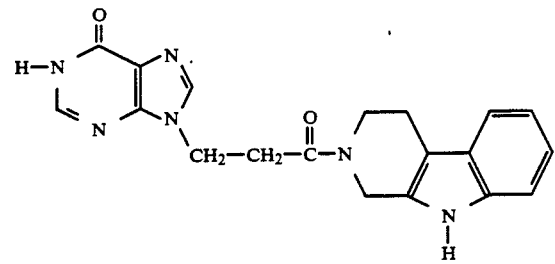

AIT-0099 3-(1,6-dihydro-6-oxo-9H-purin-9-yl)-1-(1,2,3,4-tetrahydro-2-azacarbazo-2-yl)propanone -continued

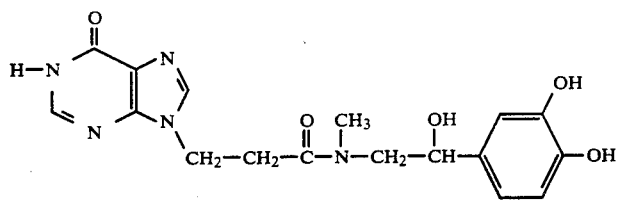

AIT-0100 3-(1,6-dihydro-6-oxo-9H-purin-9-yl)-N-[2-(3,4-dihydroxphenyl)-2-hydroxyethyl]-N-methylpropanamide

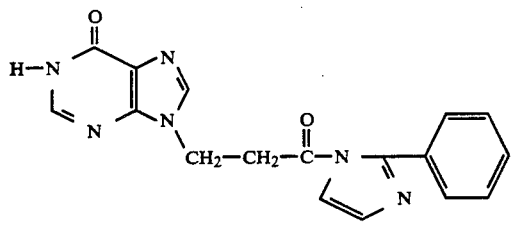

AIT-0102 3-(1,6-dihydro-6-oxo-9H-purin-9-yl)-1-(2-phenylimidazo-1-yl)propanone

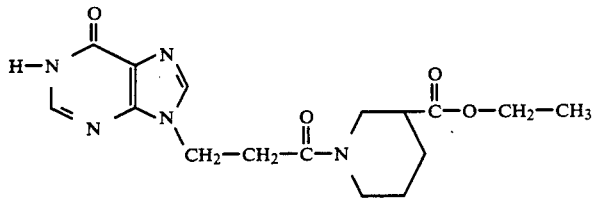

AIT-0103 1-[3-(1,6-dihydro-6-oxo-9H-purin-9-yl)-1-oxopropyl]-3-piperidine carboxylic acid, ethyl ester

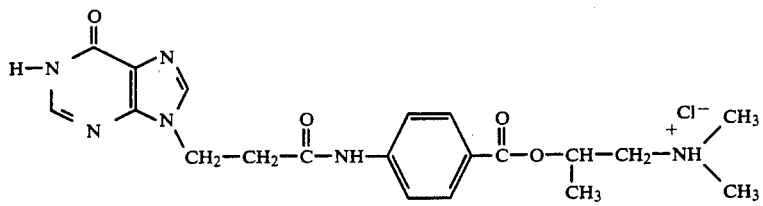

AIT-0105 4-[[3-(1,6-dihydro-6-oxo-9H-purin-9-yl)-1-oxopropyl]amino]benzoic acid,
1-(dimethylamino)-2-propyl ester, monohydrochloride

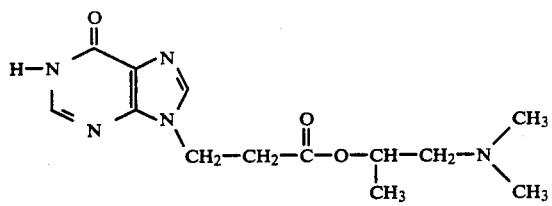

AIT-0106 3-(1,6-dihydro-6-oxo-9H-purin-9-yl)propanoic acid, 1-(dimethylamino)-2-propyl ester

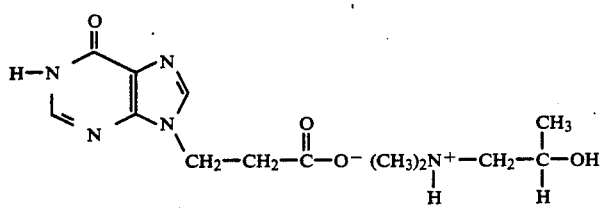

AIT-0110 3-(1,6-dihydro-6-oxo-9H-purin-9-yl)propanoic acid, cmpd. with
1-(dimethylamino)-2-propanol(1:1)

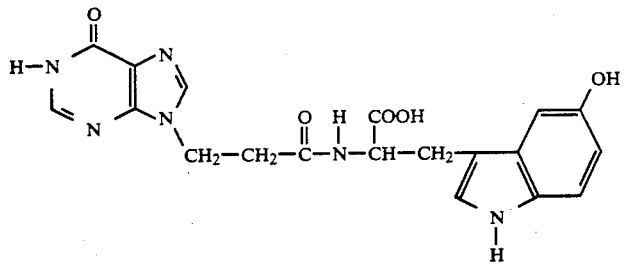

AIT-0111 2-[[3-(1,6-dihydro-6-oxo-9H-purin-9-yl)-1-oxopropyl]amino]-2-(5-hydroxyl-1H-indol-3-yl)propionic acid

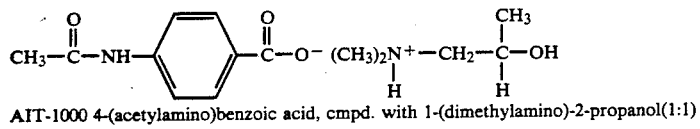

AIT-1000 4-(acetylamino)benzoic acid, cmpd. with 1-(dimethylamino)-2-propanol(1:1)

I claim:

1. A bi-functional pharmaceutical compound having neuroimmunologic properties consisting of 3-(1,6-dihydro-6-oxo-9H-purin-9-yl)-N-propanamide.

2. A bi-functional pharmaceutical compound having neuroimmunologic properties consisting of 3-(1,6-dihydro-6-oxo-9H-purin-9-yl)-N-[2-[[2-(2-oxo-1-pyrrolidinyl)-1-oxoethyl]amino]ethyl]propanamide.

3. A bi-functional pharmaceutical compound having neuroimmunologic properties consisting of 4-[[3-(1,6-dihydro-6-oxo-9H-purin-9-yl)-1-oxopropyl]amino]benzoic acid.

4. A bi-functional pharmaceutical composition having neuroimmunologic properties consisting of 4-[[3-(1,6-dihydro-6-oxo-9H-purin-9-yl)-1-oxopropyl]amino]benzoic acid compounded with 1-(dimethylamino)-2-propanol in an approximately 1 to 1 ratio.

5. A bi-functional pharmaceutical composition having neuroimmunologic properties consisting of 3-(1,6-dihydro-6-oxo-9H-purin-9-yl)propanoic acid compounded with 1-(dimethylamino)-2-propanol in an approximately 1 to 1 ratio.

6. A method for the treatment of neuroimmunologic disorder in a mammal suffering therefrom, said method comprising the step of administrating an effective amount of the compound of claim 1.

7. A method for the treatment of neuroimmunologic disorder in a mammal suffering therefrom, said method comprising the step of administrating an effective amount of the compound of claim 2.

8. A method for the treatment of neuroimmunologic disorder in a mammal suffering therefrom, said method comprising the step of administrating an effective amount of the compound of claim 3.

9. A method for the treatment of neuroimmunologic disorder in a mammal suffering therefrom, said method comprising the step of administrating an effective amount of the composition of claim 4.

10. A method for the treatment of neuroimmunologic disorder in a mammal suffering therefrom, said method comprising the step of administrating an effective amount of the composition of claim 5.

* * * * *

UNITED STATES PATENT AND TRADEMARK OFFICE
CERTIFICATE OF CORRECTION

PATENT NO. : 5,091,432

DATED : February 25, 1992

INVENTOR(S) : Alvin J. Glasky

It is certified that error appears in the above-identified patent and that said Letters Patent is hereby corrected as shown below:

Claim 1 (column 53, lines 25 and 26), delete "3-(1,6-dihy-dro-6-oxo-9H-purin-9-yl)-N-propanamide" and substitute therefor ---3-(1,6-dihy-dro-6-oxo-9H-purin-9-yl)-N-[3-(2-oxopyrrolidin-1-yl)propyl]propanamide---.

Signed and Sealed this

Seventh Day of December, 1993

Attest:

BRUCE LEHMAN

Attesting Officer

Commissioner of Patents and Trademarks